United States Patent
Li et al.

(10) Patent No.: US 9,809,615 B2
(45) Date of Patent: Nov. 7, 2017

(54) ANTI-CANCER COMPOUNDS FROM INVASIVE SALVINIAS AND METHODS OF TREATING CANCER

(71) Applicant: STEPHEN F. AUSTIN STATE UNIVERSITY, Nacogdoches, TX (US)

(72) Inventors: Shiyou Li, Nacogdoches, TX (US); Ping Wang, Nacogdoches, TX (US); Guangrui Deng, Nacogdoches, TX (US); Wei Yuan, Nacogdoches, TX (US); Zushang Su, Nacogdoches, TX (US)

(73) Assignee: STEPHEN F. AUSTIN STATE UNIVERSITY, Nacogdoches, TX (US)

(*) Notice: Subject to any disclaimer, the term of this patent is extended or adjusted under 35 U.S.C. 154(b) by 15 days.

(21) Appl. No.: 14/770,780

(22) PCT Filed: Feb. 17, 2014

(86) PCT No.: PCT/US2014/016724
§ 371 (c)(1),
(2) Date: Aug. 26, 2015

(87) PCT Pub. No.: WO2014/133811
PCT Pub. Date: Sep. 4, 2014

(65) Prior Publication Data
US 2016/0002279 A1 Jan. 7, 2016

Related U.S. Application Data

(60) Provisional application No. 61/769,506, filed on Feb. 26, 2013.

(51) Int. Cl.
| | |
|---|---|
| *A61K 31/05* | (2006.01) |
| *A61K 45/06* | (2006.01) |
| *C07H 17/08* | (2006.01) |
| *C07C 49/747* | (2006.01) |
| *C07C 39/17* | (2006.01) |
| *C07C 49/755* | (2006.01) |
| *C07C 49/737* | (2006.01) |
| *A61K 31/11* | (2006.01) |
| *A61K 31/122* | (2006.01) |
| *A61K 31/7048* | (2006.01) |
| *C07C 47/57* | (2006.01) |

(52) U.S. Cl.
CPC ............ *C07H 17/08* (2013.01); *A61K 31/05* (2013.01); *A61K 31/11* (2013.01); *A61K 31/122* (2013.01); *A61K 31/7048* (2013.01); *A61K 45/06* (2013.01); *C07C 39/17* (2013.01); *C07C 47/57* (2013.01); *C07C 49/737* (2013.01); *C07C 49/747* (2013.01); *C07C 49/755* (2013.01)

(58) Field of Classification Search
CPC .................................................. A61K 31/05
See application file for complete search history.

(56) References Cited

U.S. PATENT DOCUMENTS

2010/0022632 A1* 1/2010 Hsiao .................. A61K 31/122
514/455

OTHER PUBLICATIONS

Fronza et al., Bioorg. Med. Chem., 2011, 19, p. 4876-4881.*
Borja-Cacho et al., J. Gastrointest. Surg., 2010, 14, p. 252-260.*
Abbasi et al., "Infestation by aquatic weeds of the fern genus Salvinia: its status and contro," *Environ Conserv.* vol. 13, 1986, pp. 235-241.
Areche et al., "Gastroprote ctive effect and cytotoxicity of abietanediterpenes from the Chilean Lamiaceae Sphacelechamaedryoides (Balbis) Briq.," J Pharm Pharmacol, vol. 61, No. 12, 2009, pp. 1689-1697.
Arihara et al., "A New Abietane and Two Dimeric Abietane Diterpenes from the Black Heartwood of Cryptomeria japonica," Chem Pharm Bull. vol. 52, No. 3, 2004, pp. 354-358.
Avupati et al., "Synthesis, characterization and in vitro and biological evaluation of some novel diarylsulfonylureas as potential cytotoxic and antimicrobial agents," Bioorg Med Chem Lett. vol. 22, No. 2, 2012, pp. 1031-1035.
Bang et al., "13-Hydroxy-9Z,11E,15E-octadecatrienoic acid from the leaves of Cucurbita moschata," Arch Pharm Res. vol. 25, No. 4, 2002, 438-440.
Barrett et al., "Waterweed invasions," Sci Amer. vol. 260, 1989, pp. 90-97.
Brubaker et al., "Synthesis and rat lens aldose reductase inhibitory activity of some benzopyran-2-ones," J Med Chem. vol. 29, No. 6, 1986, 1094-1099.
Chantiratikul et al., "Antioxidant Activities and Phenolic Contents of Extracts from Salvinia molesta and Eichornia crassipes," Res J Biol Sci. vol. 4, No. 10, 2009, pp. 1113-1117.
Choudhary et al., "Phenolic and other constituents of fresh water fern Salvinia molesta," Phytochemistry. vol. 69, No. 4, 2008, pp. 1018-1023.
Dellagreca et al., "Isolation and phytotoxicity of apocarotenoids from Chenopodium album," J Nat Prod. vol. 67, No. 9, 2004, 1492-1495.
Ding et al., "Glycosides from Paeonia suffruticosa," Chem Pharm Bull. vol. 47, No. 5, 1999, pp. 652-655.
Elisa et al., Annali di Chimica, 59(6):510-7, 1969.
Fang et al., J Chem Res-S. 9:350-1, 1986.
Fielding et al., J Chem Soc. 2(1):151-63, 2002.
Fraga et al., "Diterpenes from Salvia broussonetii Transformed Roots and Their Insecticidal Activity," J Agric Food Chem. vol. 53, No. 13, 2005, pp. 5200-5206.
Fujita et al., "Two Jasmonoid Glucosides and a Phenylvaleric Acid Glucoside from Perilla frutescens," Biosci Biotech Biochem. vol. 60, No. 4, 1996, pp. 732-735.

(Continued)

Primary Examiner — Jonathan S Lau
(74) Attorney, Agent, or Firm — Norton Rose Fulbright US LLP

(57) ABSTRACT

Compositions and methods related to anti-cancer terpenoid compounds isolated from plants in the Salviniaceae family, pharmaceutical compositions comprising the same, and methods of treating cancer.

8 Claims, 4 Drawing Sheets

(56) References Cited

OTHER PUBLICATIONS

Gonzalez et al., "Short synthesis of (+)-ferruginol from (+)-dehydroabietylamine?" Tetrahedron. vol. 68, 2012, pp. 9612-9615.
Guerrero et al., "Abietane diterpenoids from Salvia pachyphylla and S. clevelandii with cytotoxic activity against human cancer cell lines," J Nat Prod. vol. 69, No. 12, 2006, pp. 1803-1805.
Hsieh et al., "$C_{35}$ terpenoids from the bark of *Calocedrus macrolepis* var. formosana with activity against human cancer cell lines," J Nat Prod. vol. 69, No. 11, 2006, pp. 1611-1613.
Huang et al., "Three Novel Terpenoids from *Schisandm pubescens* var. pubinervis," Helv Chim Acta. vol. 89, No. 6, 2006, pp. 1169-1175.
International Preliminary Report on Patentability in International Application No. PCT/US2014/016724 dated Sep. 11, 2015.
International Search Report and Written Opinion in International Application No. PCT/US2014/016724 dated Nov. 20, 2014.
Jonathan et al., "7-O-methylhorminone and other cytotoxic diterpene quinones from Lepechinia bullata," J Nat Prod. vol. 52, No. 3, 1989, pp. 571-575.
Katoh et al., "Synthesis of DL-standishinal and its related compounds for the studies on structure-activity relationship of inhibitor activity against aromatase" Bioorganic and Medicinal Chemistry. vol. 15, 2007, pp. 2736-2748.
Knöfel et al., "Jasmonates from pine pollen," Phytochemistry. vol. 38, No. 3, 1995, pp. 569-571.
Kuo et al., "New Dimeric Monoterpenes and Dimeric Diterpenes from the Heartwood of *Chamaecyparis obtusa* var. formosana," Helv Chim Acta. vol. 85, No. 9, 2002, pp. 2657-2663.
Kuo et al., "Norditerpenes from the heartwood of Picea morrisonicola," Phytochemistry, vol. 49, No. 8, 1998, pp. 2453-2455.
Kusumoto et al., "Antitermitic Activities of Abietane-type Diterpenes from Taxodium distichum Cones," J Chem Ecol. vol. 35, No. 6, 2009, pp. 635-642.
Li et al., "Cytotoxic compounds from invasive giant salivinia (Salvinia molesta) against human tumor cells" Bioorganic and Medicine Chemistry Letterss. vol. 23, 2013, pp. 6682-6687.
Li et al., "Synthesis of C7 oxidized abietane diterpenes from racemic ferruginyl methyl ether" Tetrahedron vol. 59, 2003, pp. 5737-5741.
Lin et al., "A novel diterpene suppresses CWR22Rv1 tumor growth in vivo through antiproliferation and proapoptosis," Cancer Res. vol. 68, No. 16, 2008, pp. 6634-6642.
Mahato et al., "$^{13}C$ NMR Spectra of pentacyclic triterpenoids—a compilation and some salient features," Phytochemistry. vol. 37, No. 6, 1994, pp. 1517-1575.
Miyazawa et al., "Biotransformations of Acyclic Terpenoids, (±)-trans-Nerolidol and Geranylacetone, by Glomerella cingulate," J Agric Food Chem. vol. 44, No. 6, 1996, pp. 1543-1547.
Moozhiyil et al., "Chemical composition of the water fern,salvinia molesta, and its potential as feed source for ruminants," J Econ Bot. vol. 40, No. 3, 1986, pp. 375-383.
Moujir et al., "Bioactive Diterpenoids Isolated from Salvia mellifera," Phytotherapy Res. vol. 10, No. 2, 1996, pp. 172-174.
Mustafa et al., "Experiments with substituted (3,2-c)-pyranyl-2,10-diones and benzopyranyl-(3,2-c) pyran-2,8-diones," Tetrahedron. vol. 19, No. 11, 1963, pp. 1831-1839.
Narasimhulua et al., "An unusual novel anti-oxidant dibenzoyl glycoside from Salvinia natans," Nat Prod Res. vol. 24, No. 15, 2010, pp. 1390-1394.
Oiso et al., "Hymenosides A-F, six new hemiterpene glucosides from the Japanese fern Hymenophyllum barbatum," Chem. Pharm. Bull. vol. 49, No. 1, 2001, pp. 126-128.

Rodriguez, "$^1H$ and $^{13}C$ NMR spectral assignments of some natural abietane diterpenoids," Magn Reson Chem. vol. 41, No. 9, 2003, 741-746.
Room et al., "Population Growth of the Floating Weed Salvinia molesta: Field Observation and a Global Model Based on Temperature and Nitrogen," J Appl Ecol. vol. 23, No. 3, 1986, pp. 1013-1028.
Sairafianpour et al., "Leishmanicidal, Antiplasmodial, and Cytotoxic Activity of Novel Diterpenoid 1,2-Quinones from Perovskia abrotanoides: New Source of Tanshinones," J Nat Prod. vol. 64, No. 11, 2001, pp. 1398-1403.
Schooler et al., "Alternative stable states explain unpredictable biological control of Salvinia molesta in Kakadu," Nature, vol. 470, 2011, pp. 86-89.
Siddiqui et al., "Chemical constituents of Centella asiatica," J Asian Nat Prod Res. vol. 9, No. 4, 2007, pp. 407-414.
Slamenova et al., "Cytotoxic and DNA-damaging effects of diterpenoid quinones from the roots of *Salvia officinalis* L. on colonic and hepatic human cells cultured in vitro," Basic Clin Pharmacol Toxicol. vol. 94, No. 6, 2004, pp. 282-290.
Srilaxmi et al., "Protective efficacy of natansnin, a dibenzoyl in glycoside from Salvinia natans against CC14 induced oxidative stress and cellular degeneration in rat liver," BMC Pharmacol. vol. 10:13, 2010, 13 pages.
Tamura et al., "Unprecedented NES non-antagonistic inhibitor for nuclear export of Rev from Sida cordifolia," Bioorg Med Chem Lett. vol. 20, No. 6, 2010, pp. 1837-1839.
Tan et al., "Secondary metabolites from Pandanus simplex," Biochem Syst Ecol. vol. 40, 2012, pp. 4-5.
Tanaka et al., "Facile discrimination of aldose enantiomers by reversed-phase HPLC," Chem. Pharm. Bull. vol. 55, No. 6, 2007, pp. 899-901.
Tezuka et al., "Constituents of Roots of Salvia deserta," Chem Pharm Bull. vol. 46, No. 1, 1998, pp. 107-112.
Topcu et al., "Cytotoxic Activity of Some Anatolian Salvia. Extracts and Isolated Abietane Diterpenoids," Pharm Biol, vol. 46, No. 3, 2008, pp. 180-184.
Toyota et al., "New Glycosides from the Japanese Fern Hymenophyllum barbatum," Chem. Pharm. Bull. vol. 50, No. 4, 2002, pp. 508-514.
Ulubelen et al., "Cytotoxic Activity of Diterpenoids Isolated from Salvia hypargeia," Pharma Biol. vol. 37, No. 2, 1999, pp. 148-151.
Ulubelen et al., "New Abietane Diterpenoids from Salvia montbretii," J Nat Prod. Vol, 55, No. 4, 1992, pp. 441-444.
Wu et al., "New sesquiterpene and triterpene from the fruits of Cryptomeria fortune," J Asian Nat Prod Res. vol. 12, No. 5, 2010, pp. 382-387.
Xiang et al., "A New Abietane Diterpenoid from Orthosiphon wulfenioides," Chinese Chem Lett. vol. 13, No. 2, 2002, pp. 141-142.
Xiang et al., "Two new components from Gnetum pendulum," J Asian Nat Prod Res. vol. 10, No. 11, 2008, pp. 1081-1085.
Yao et al., "Abietane Diterpenoids from the Bark of Cryptomeria fortune," J Nat Prod. vol. 71, No. 7, 2008, pp. 1242-1246.
Yoshikawa et al., "Abietane diterpenoids from the barks of Cryptomeria japonica," Chem Pharm Bull. vol. 54, No. 4, 2006, pp. 574-578.
Yoshikawa et al., "Three Abietane Diterpenes and Two Diterpenes Incorporated Sesquiterpenes from the Bark of Cryptomeria japonica ," Chem Pharm Bull. vol. 54, No. 3, 2006, pp. 315-319.
Zhang et al., "Phenolic compounds and rare polyhydroxylated triterpenoid saponins from Eryngium yuccifolium," Phytochemistry. vol. 69, No. 10, 2008, pp. 2070-2080.
Zhao et al., "Bioactive compounds from the aerial parts of Brachystemma calycinum and structural revision of an octacyclopeptide," J Nat Prod. vol. 74, No. 6, 2011, pp. 1392-1400.

\* cited by examiner

ANTI-CANCER COMPOUNDS FROM INVASIVE SALVINIAS AND METHODS OF TREATING CANCER

CROSS-REFERENCE TO RELATED APPLICATION

This application is a national phase application under 35 U.S.C. §371 of International Application No. PCT/US2014/016724, filed Feb. 17, 2014, which claims the benefit of priority of U.S. Provisional Patent Application No. 61/769,506, filed on Feb. 26, 2013, The entire contents of each of the above-referenced disclosures are specification incorporated herein by reference without disclaimer.

GOVERNMENT LICENSE RIGHTS

This invention was made with government support under grant number 2008-38928-19308 awarded by the U.S. Department of Agriculture. The government has certain rights in this invention.

BACKGROUND OF THE INVENTION

A. Field of the Invention

The invention generally relates to compositions derived from plants and pharmaceutical uses thereof. In particular, the invention relates to the use of bioactive composition isolated from plants in the Salviniaceae family.

B. Description of Related Art

Giant *salvinia* (*Salvinia molesta* D. S. Mitchell) is one of the most widespread and environmentally, economically and socially destructive invasive plant species in the world. The *salvinia* also provides habitat for snails that are intermediate hosts for *Schistosoma* sp. which causes parasitic disease Schistosomiasis, the second most socioeconomically devastating parasitic disease after malaria. To date, control measures, particularly biological and chemical methods of this invasive species are very expensive and have failed to achieve their purpose and may cause environmental backlashes. Positive control by harvesting and utilizing giant *salvinia* has never been developed.

Therefore, new beneficial uses and positive control methods for these plants are needed.

SUMMARY OF THE INVENTION

In some embodiments, the compositions and methods disclosed herein relate to compounds isolated from plants in the Salviniaceae family, compositions comprising the same, and methods of using the same.

In one aspect, there are provided compounds of the formula:

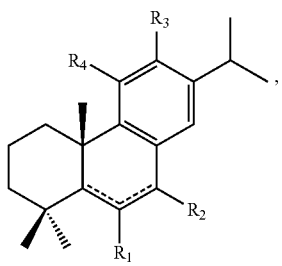

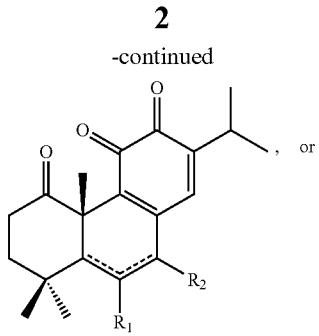

wherein $R_1$ is H, OH, OCH$_3$, or =O; $R_2$ is H, OH, OCH$_3$, or =O; $R_3$ is H, OH, or OCH$_3$; and $R_4$ is H, or OH.

In one aspect, there are provided compounds of the formula:

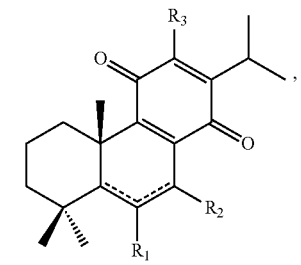

wherein $R_1$ and $R_2$ are, independently, CHO, CH$_3$OH, or COOH.

In embodiments, the compounds are further defined as:

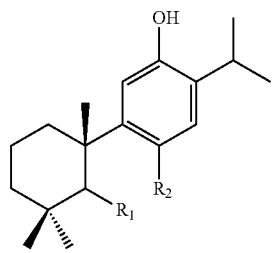

In one aspect, there are provided compounds of the formula:

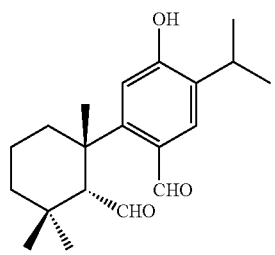

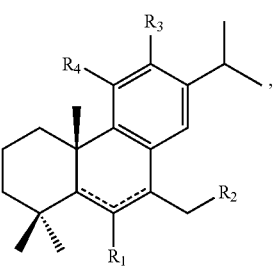
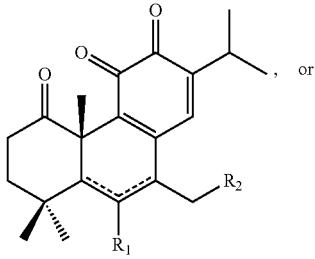, or
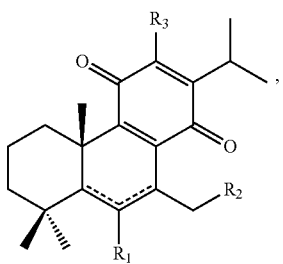
wherein $R_1$ is H, OH, OCH$_3$, or =O; $R_3$ is H, OH, or OCH$_3$; $R_4$ is H or OH; and $R_2$ is:
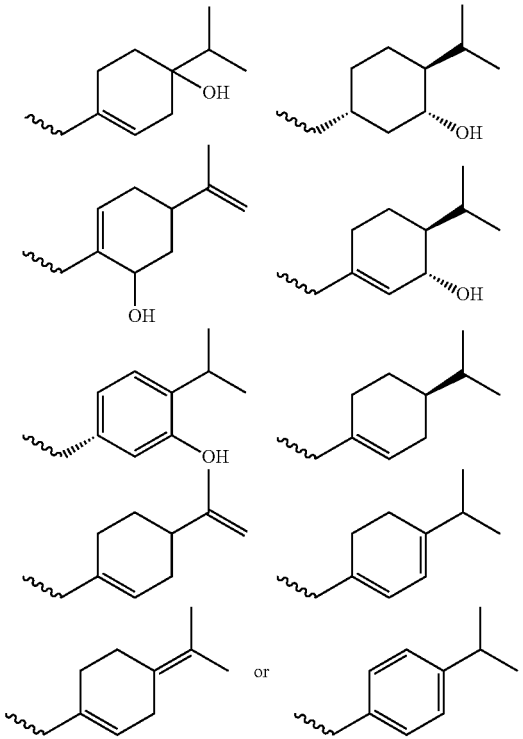
In embodiments, the compounds are further defined as:
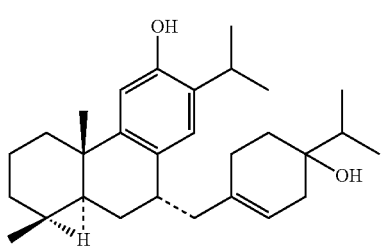
In one aspect, there are provided compounds of the formula:
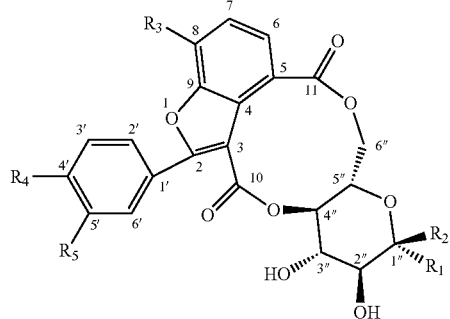
wherein R1 is one of:
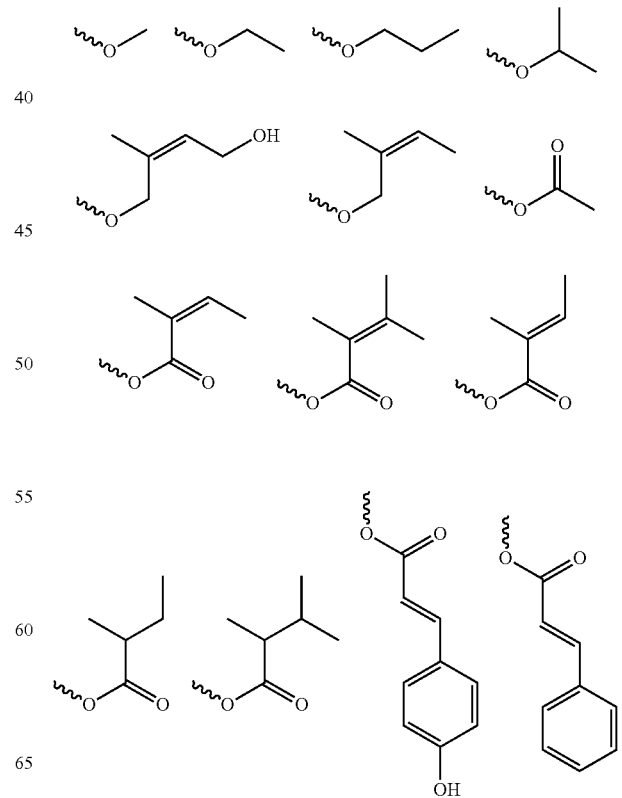

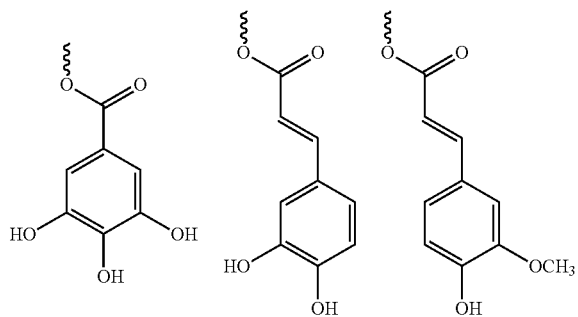

$R_2$ is H or OH; and $R_3$, $R_4$, and $R_5$ are each, independently, H, OH, or OMe.

In embodiments, the compounds are further defined as:

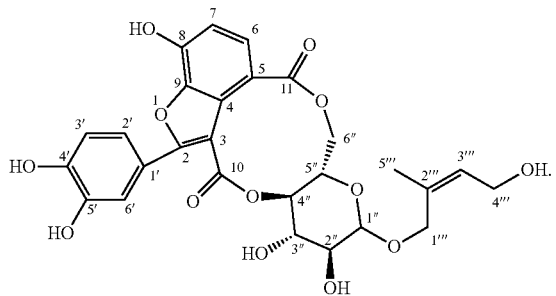 [SMILES: C/C(=C/CO)COC1O[C@H]2COC(=O)c3ccc(O)c4oc(-c5ccc(O)c(O)c5)c(c34)C(=O)O[C@@H]2[C@@H](O)[C@@H]1O]

In embodiments, the compounds are further defined as:

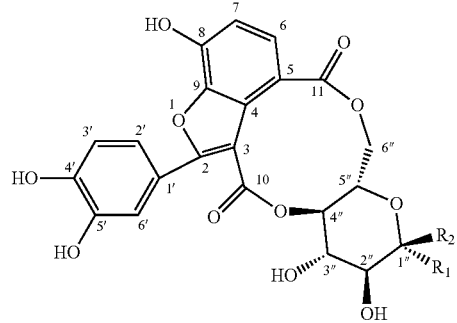

wherein $R_1$ is α-H or OH; and $R_2$ is β-H or OH.

In one aspect, there are provided compounds of the formula:

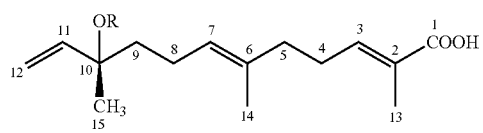

wherein R is β-D-glucopyranosyl or H.

In one aspect, there are provided compounds of the formula:

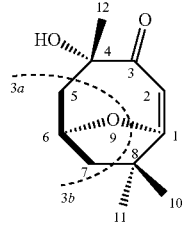

In one aspect, there are provided compounds of the formula:

In some aspects, the compound is isolated from a plant in the Salviniaceae family. In some embodiments, the compound is isolated from a plant in the *Salvinia* genus. In some embodiments, the compound is isolated from *S. auriculata, S. biloba, S. cucullata, S. cyathiformis, S. hastate, S. herzogii, S. minima, S. molesta, S. natans, S. nymphellula, S. oblongifolia, S. radula, S. rotundifolia,* or *S. sprucei*. In some embodiments, the compound is isolated from a plant in the *Azolla* genus.

In some aspects, there are provided pharmaceutical compositions comprising one or more of the above compounds and an excipient. In other aspects there are provided methods of treating cancer in patients in need thereof, comprising administering to such patients one or more of the above compounds in an amount sufficient to treat the cancer.

As used herein, the term "patient" or "subject" refers to a living mammalian organism, such as a human, monkey, cow, sheep, goat, dogs, cat, mouse, rat, guinea pig, or transgenic species thereof. In certain embodiments, the patient or subject is a primate. Non-limiting examples of human subjects are adults, juveniles, infants and fetuses. In some embodiments, the patient is a human.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treating cancer is further defined as reducing the size of a tumor or inhibiting growth of a tumor.

The compounds may be administered by any acceptable route. In some embodiments, the compounds are administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof.

The cancer may be any cancer. In some embodiments, the cancer is melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplastic syndrome, multiple myeloma, transitional cell carcinoma, neuroblastoma, plasma cell neoplasms, Wilm's tumor, or hepatocellular carcinoma. In some embodiments, the cancer is pancreatic cancer, leukemia, lung cancer, breast cancer, or prostate cancer.

The compositions may be administered one or more times. In some embodiments, the compositions are administered 1, 2, 3, 4, 5, 6, 7, 8, 9, or 10 times or more.

The methods of the present invention may be used in combination with additional cancer therapy. In some embodiments, the distinct cancer therapy comprises surgery, radiotherapy, chemotherapy, toxin therapy, immunotherapy, cryotherapy or gene therapy. In some embodiments, the cancer is a chemotherapy-resistant or radio-resistant cancer.

"Effective amount" or "therapeutically effective amount" or "pharmaceutically effective amount" means that amount which, when administered to a subject or patient for treating a disease, is sufficient to effect such treatment for the disease. In some embodiments, the subject is administered at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, or 100 mg/kg (or any range derivable therein).

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., *Verlag Helvetica Chimica Acta,* 2002).

In some aspects, there are provided methods of treating liver or cardiac disease in a patient in need thereof, comprising administering to the patient one or more of the above compounds in an amount sufficient to treat the liver or cardiac disease.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The use of the word "a" or "an" when used in conjunction with the term "comprising" may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A Effect of salviniol (6) on the proliferation of human exocrine pancreatic cancer cells (BxPC-3). FIG. 3B Effect of montbretol (8) on the proliferation of human exocrine pancreatic cancer cells (BxPC-3). FIG. 3C Effect of salviniol (6) on the proliferation of human exocrine pancreatic cancer cells (PANC-1). FIG. 3D Effect of montbretol (8) on the proliferation of human exocrine pancreatic cancer cells (PANC-1).

DESCRIPTION OF ILLUSTRATIVE EMBODIMENTS

Figure 1:
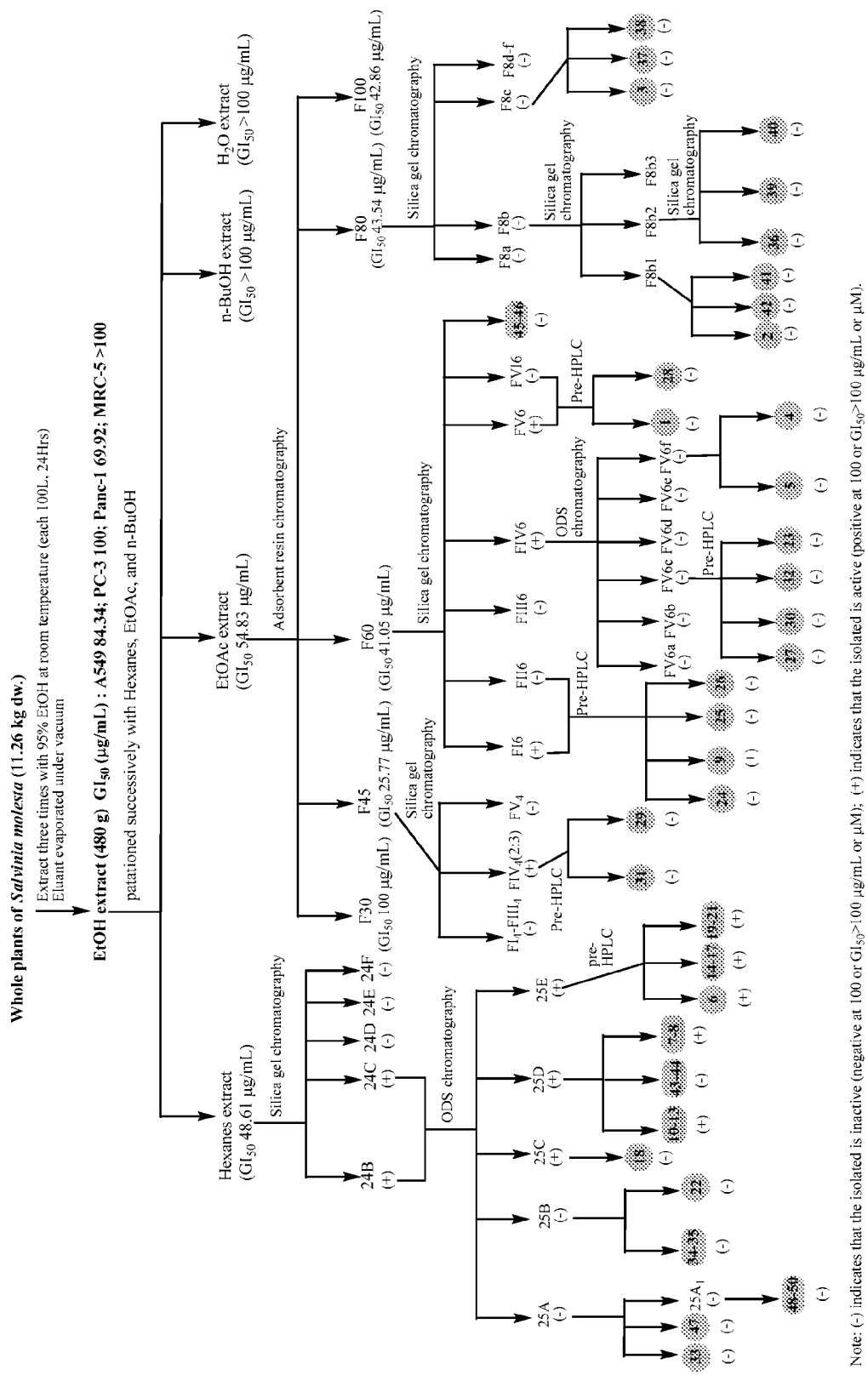
FIG. 1. Bioassay guided isolation procedure of *Salvinia molesta*.

The ethanol extract of giant *salvinia* and other *salvinia* species shows promising activity to control human tumor growth with less toxicity to normal cells in vitro. The inventors have isolated over 50 compounds from the plants including six new compounds and identified a class of bioactive compounds. These compounds showed in vitro bioactivity against non-small cell lung cancer (A549 (human lung adenocarcinoma epithelial cell line)), prostate cancer (PC-3 (human prostate adenocarcinoma epithelial cell line)), pancreatic cancer (non-endocrine PANC-1 (human exocrine pancreatic carcinoma) and exocrine BxPC-3 (human exocrine pancreatic carcinoma)), breast cancer (MDA-MB-231 (human breast adenocarcinoma epithelial cell line)), and leukemia (HL-60 (human promyelocytic leukemia cell line)) cells.

The bioactive compounds, particularly the new compound salviniol (6) (a rare abietane diterpene with a new ferruginol-menthol coupled skeleton) isolated from giant *salvinia* provide lead compounds in the drug development for cancer and inflammation treatment. Pharmaceutical production of bioactive agents from *salvinia* will provide the best way to "control" the most noxious invasive species.

A. SALVINIACEAE

Salviniaceae is a family of heterosporous ferns in the order Salviniales. The Salviniaceae contain the two genera *Azolla* and *Salvinia*.

*Azolla*, also known as mosquito fern, duckweed fern, fairy moss, water fern, is a genus of seven species of aquatic ferns. They are extremely reduced in form and specialized, looking nothing like conventional ferns but more resembling duckweed or some mosses.

*Salvinia* Ség. is a genus of floating ferns having 10-14 species in the world, particularly in the tropics. *Salvinia molesta* D. S. Mitchell, known as giant *salvinia*, water fern, or kariba weed, is native to Brazil. Since 1939, it has invaded lake and river systems in warm climates in the world (Room, 1990). At present, giant *salvinia* is one of the most widespread and environmentally, economically and socially destructive invasive plant species (Schooler, 2011). In addition, giant *salvinia* provides habitat for snails that are intermediate hosts for *Schistosoma* sp. which parasitize the human intestinal and urinary tracts. The parasitic disease Schistosomiasis is also known as snail fever, bilharzia, or bilharziosis, is the second most socioeconomically devastating parasitic disease after malaria.

Giant *salvinia* is able to double in number and biomass in less than three days under optimal condition and forms dense mats over still waters (Barrett, 1989). The plant can regenerate vegetatively even after severe damage or drying for days (Room, 1986; Finlayson, 1984). The explosive growth of *S. molesta* does not only affect adversely the natural ecological system of the infested region but also cause considerable economic damage and sanitation problems. Dense mats of *S. molesta* reduce dissolved oxygen levels and block all sunlight from penetrating the infested water body. Thus, macrophytes and microscopic algae that form the base of the food chain may die off (Room, 1990; USDA: Giant *Salvinia*-Pest Alert). The creatures that feed on these may die, too, and so on up the food chain. This pest threatens cultivated aquatic crops, and it can clog irrigation and drinking water lines and foul hydroelectric plants. *Salvinia* infested waters cannot be used for boating or other recreational purposes (USDA: Giant *Salvinia*-Pest Alert).

Since 1980, the tiny *salvinia* weevil (*Cyrtobagous salviniae*, Curculionidae) has been introduced into most regions where giant *salvinia* has invaded (Julien, 2009). The weevil is a strict specialist with adults feeding on *salvinia* buds while the plant is highly susceptible to the insects and thus the weevil has successfully controlled *salvinia* for years in some regions. But recently it was found that the biological control is incomplete and fitful associated with stochastic flooding events and thus is unpredictable (Schooler, 2011). Other attempts to control and eradicate *S. molesta* through chemical and mechanical means have failed to achieve their purpose and may cause environmental backlashes being caused by the introduction of chemicals or bioagents into the environment (Abbasi, 1986).

Researchers had analysed the chemical composition of giant *salvinia* to evaluate its suitability as a source of forage for ruminants but the high content of crude ash, lignin and tannins restrict the use (Moozhiyil, 1986). Recently, it was found that *salvinia* is able to accumulate certain metals makes it potentially useful for waste management and effluent treatment (Choudhary, 2008). Positive control by harvesting and utilizing giant *salvinia* has not been developed, and the medical or pharmaceutical potential of giant *salvinia* remains unexplored. Most studies on cancer drug discovery have been prioritized on non-common plant species, and no species of the genus *Salvinia* or family Salviniaceae has been previously reported to have anti-tumor activity.

Previous phytochemical investigations reported six phenolics, one iridiod, and one terpenoid in the *Salvinia* genus and some compounds showed antioxidant activity (Choudhary, 2008; Srilaxmi, 2010; Chantiratikul, 2009; Narasimjulua, 2010).

B. THERAPEUTIC COMPOUNDS

A crude ethanol extract of *S. molesta* showed moderate cytotoxic activity against human non-small cell lung cell (A549), human prostate cancer cell (PC-3), and human pancreatic cancer cell (PANC-1) but not toxic to normal human lung fibroblasts cells (MRC-5). A bioactivity-guided fractionation of ethanol extracts of giant *salvinia* led to the isolation of 50 compounds including 17 abietane diterpenes (6-22), nine phenolics (2, 4, 5, 27-30, 43, and 44), four apocavotenoids (36-39), five unsaturated hydroxyl fatty acids (24-26, 45, and 46), two acyclic sesquiterpenoids (1 and 23), two monoterpenes (3 and 40), two jasmonates (31 and 32), two steroids (34 and 35), two coumarins (41 and 42), and five triterpenes (33, and 47-50). All abietane diterpenes were isolated from *Salvinia* for the first time. Their structures were elucidated by spectroscopic data interpretation. Among the 50 compounds, six are new compounds (1-6). Salviniol [7-(menth-1-en-4-ol)-ferruginol] (6) is a rare abietane diterpene with a ferruginol-menthol coupled skeleton.

Cytotoxicity of 50 compounds against human cancer cell lines was examined in vitro. Among all compounds, 16 abietane diterpenes (6-17 and 19-22) demonstrated activities against human non-small cell lung cancer (A549), prostate cancer (PC-3), exocrine pancreatic cancer (PANC-1 and BxPC-3), breast cancer (MDA-MB-231), and leukemia (HL-60) cells and normal human lung fibroblasts MRC-5. The bioactivities of compounds 6, 11, 15, 16, 17, and 22 were reported for the first time. The bioactivities of compounds 7, 8, 12, 20, and 21 against human exocrine pancreatic cancer have never been reported before. It is also the first report of the selective activities of compounds 7 and 8 to human non-small cell lung cancer (A549) but less toxic normal human lung fibroblasts MRC-5. The cytotoxicity of compounds 12 and 21 against human non-small cell lung cancer (A549), prostate cancer (PC-3), and leukemia (HL-60) are reported for the first time. See Table 1.

Based on the structure-activity relationship analysis of bioactive compounds, the abietane diterpenes with group "OH", "OCH$_3$" or "=O" at C-12 have potent cytotoxicity against human tumors, and abietane diterpenes also have one of these groups at C-6 will enhance the bioactivity. 6,7-seco abietane derivatives possess cytotoxicity, but show less activity than the regular abietanes according to the bioassay results.

TABLE 1

| No. | Name | Structure | Characteristics and Activity |
|---|---|---|---|
| 6 | Salviniol (7-(menth-1-en-4-ol)-ferruginol) | (structure) | A rare abietane diterpene with a new ferruginol-menthol coupled skeleton<br>1. Activity against human exocrine pancreatic tumor PANC-1 ($GI_{50}$ = 60.44 ± 16.17 μM) and BxPC-3 ($GI_{50}$ = 87.28 ± 24.51 μM)<br>2. Activity against human non-small cell lung tumor A549 ($GI_{50}$ = 62.91 ± 9.63 μM)<br>3. Activity against human prostate tumor PC-3 ($GI_{50}$ = 54.19 ± 5.90 μM)<br>4. Activity against human leukemia HL-60 ($GI_{50}$ = 48.05 ± 10.86 μM)<br>5. Activity against human breast tumor MDA-MB-231 ($GI_{50}$ = 75.0 ± 1.37 μM) |
| 7 | 14-Deoxycoleon U | (structure) | 1. Activity against human exocrine pancreatic tumor PANC-1 ($GI_{50}$ = 22.59 ± 4.18 μM) and BxPC-3 ($GI_{50}$ = 37.28 ± 7.44 μM)<br>2. The compound is less toxic to normal human lung fibroblasts MRC-5 ($GI_{50}$ = 24.75 ± 4.73 μM)<br>than to human non-small cell lung tumor A549 ($GI_{50}$ = 9.10 ± 2.47 μM)<br>3. This compound is selective and has no activity to breast tumor (MDA-MB-231, $GI_{50}$ > 100 μM) |
| 8 | Montbretol | (structure) | 1. Activity against human exocrine pancreatic tumor PANC-1 ($GI_{50}$ = 23.08 ± 9.16 μM) and BxPC-3 ($GI_{50}$ = 25.0 ± 13.19 μM)<br>2. The compound is less toxic to normal human lung fibroblasts MRC-5 ($GI_{50}$ = 20.01 ± 5.14 μM)<br>than to human non-small cell lung tumor A549 ($GI_{50}$ = 11.07 ± 3.16 μM) |
| 9 | 5,6-Dehydrosugiol | (structure) | 1. Activity against human non-small cell lung tumor A549 ($GI_{50}$ = 84.52 ± 18.73 μM) |

TABLE 1-continued

| No. | Name | Structure | Characteristics and Activity |
|---|---|---|---|
| 10 | 7-Methoxyrosmanol | 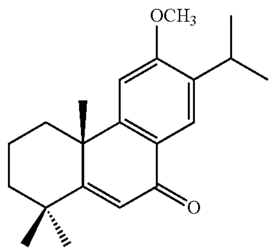 | 1. Activity against human non-small cell lung tumor A549 ($GI_{50}$ = 86.50 ± 9.54 μM) |
| 11 | Montbretyl 12-methyl ether | 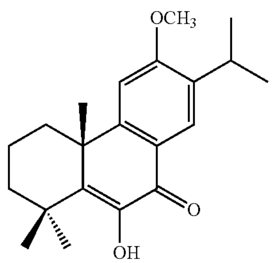 | 1. Activity against human non-small cell lung tumor A549 ($GI_{50}$ = 21.21 ± 6.21 μM) |
| 12 | 11-Hydroxysugiol | 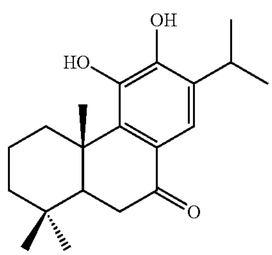 | 1. Activity against human exocrine pancreatic tumor PANC-1 ($GI_{50}$ = 43.14 ± 8.32 μM) and BxPC-3 ($GI_{50}$ = 45.01 ± 8.33 μM)<br>2. Activity against human non-small cell lung tumor A549 ($GI_{50}$ = 35.04 ± 6.20 μM)<br>3. Activity against human prostate tumor PC-3 ($GI_{50}$ = 41.03 ± 7.90 μM)<br>4. Activity against human leukemia HL-60 ($GI_{50}$ = 35.26 ± 0.63 μM) |
| 15 | 7-Hydroxy ferruginol | 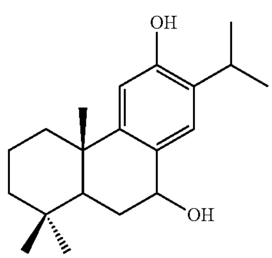 | 1. Activity against human exocrine pancreatic tumor PANC-1 ($GI_{50}$ = 78.24 ± 13.46 μM) and BxPC-3 ($GI_{50}$ = 74.73 ± 11.09 μM)<br>2. Activity against human non-small cell lung tumor A549 ($GI_{50}$ = 75.11 ± 7.04 μM)<br>3. Activity against human prostate tumor PC-3 ($GI_{50}$ = 85.61 ± 5.30 μM)<br>4. Activity against human leukemia HL-60 ($GI_{50}$ = 75.19 ± 1.02 μM) |
| 16 | 6,7-Dehydroferruginol | 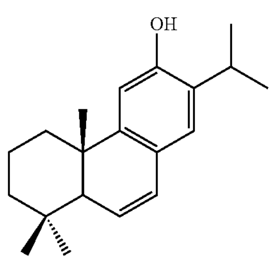 | 1. Activity against human exocrine pancreatic tumor PANC-1 ($GI_{50}$ = 46.71 ± 10.98 μM) and BxPC-3 ($GI_{50}$ = 37.50 ± 4.01 μM)<br>2. Activity against human non-small cell lung tumor A549 ($GI_{50}$ = 53.79 ± 9.65 μM)<br>3. Activity against human prostate tumor PC-3 ($GI_{50}$ = 58.12 ± 3.28 μM)<br>4. Activity against human leukemia HL-60 ($GI_{50}$ = 66.52 ± 0.04 μM) |
| 17 | 12-Hydroxy simonellite | 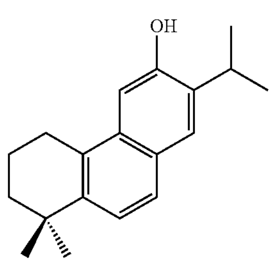 | 1. Activity against human exocrine pancreatic tumor PANC-1 ($GI_{50}$ = 37.53 ± 5.72 μM) and BxPC-3 ($GI_{50}$ = 36.42 ± 8.08 μM)<br>2. Activity against human non-small cell lung tumor A549 ($GI_{50}$ = 42.22 ± 3.89 μM)<br>3. Activity against human prostate tumor PC-3 ($GI_{50}$ = 43.60 ± 11.88 μM)<br>4. Activity against human leukemia HL-60 ($GI_{50}$ = 50.01 ± 15.23 μM) |

TABLE 1-continued

| No. | Name | Structure | Characteristics and Activity |
|---|---|---|---|
| 20 | Royleanone | 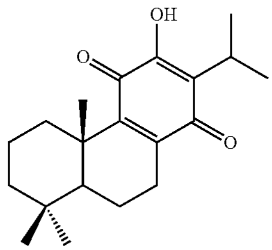 | 1. Activity against human exocrine pancreatic tumor PANC-1 ($GI_{50}$ = 52.55 ± 18.84 μM) and BxPC-3 ($GI_{50}$ = 51.04 ± 10.44 μM) |
| 21 | 6,7-Dehydroroyleanone | 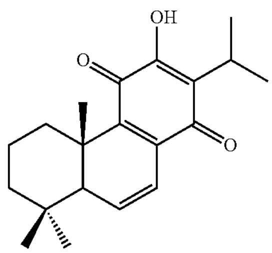 | 1. Activity against human exocrine pancreatic tumor PANC-1 ($GI_{50}$ = 51.34 ± 10.04 μM) and BxPC-3 ($GI_{50}$ = 41.74 ± 2.92 μM)<br>2. Activity against human non-small cell lung tumor A549 ($GI_{50}$ = 47.96 ± 7.75 μM)<br>3. Activity against human prostate tumor PC-3 ($GI_{50}$ = 46.32 ± 6.60 μM)<br>4. Activity against human leukemia HL-60 ($GI_{50}$ = 30.03 ± 8.30 μM) |
| 22 | 12-Hydroxy-6,7-secoabieta-8,11,13-triene-6,7-dial | 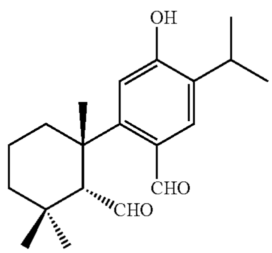 | 1. Activity against human non-small cell lung tumor A549 ($GI_{50}$ = 93.75 ± 21.39 μM) |
| 4 | Salviniside I | 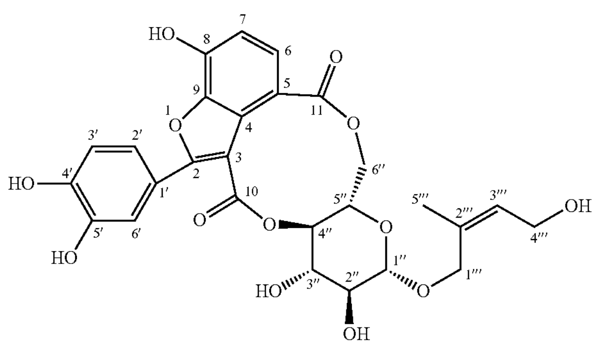 [SMILES: C/C(=C/CO)CO[C@H]1O[C@H]2COC(=O)c3ccc(O)c4oc(-c5ccc(O)c(O)c5)c(c34)C(=O)O[C@@H]2[C@@H](O)[C@@H]1O] | Novel benzofuran glucose conjugates with unique 10-membered macrodiolide structures |
| 5 | Salviniside II | 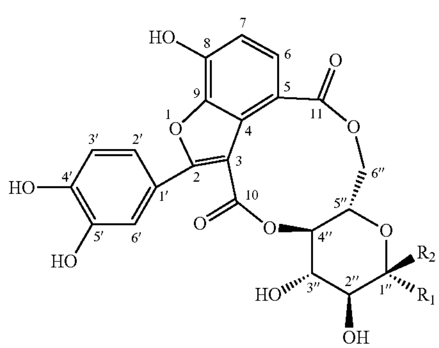 | Novel benzofuran glucose conjugates with unique 10-membered macrodiolide structures |

5 $R_1$ = OH, $R_2$ = β-H
or $R_1$ = α-H, $R_2$ = OH
5a $R_1$ = $OCH_3$, $R_2$ = H

The bioactive diterpanes isolated from *salvinias* have extremely low concentrations (ppm levels) which makes the isolation and elucidation of these compounds from *salvinias* difficult. For example, from in total 11.3 kg of dried giant *salvinia* matters (about 250 kg in fresh weight), inventors obtained only 2.0 mg of Salvinol (compound 6). The concentration of salviniol (6) in giant *salvinia* is about 0.178 ppm in dry weight. Other active compounds have similar concentrations. Therefore, such very minor compounds would be ignored by most phytochemists and would not be obtained by routine phytochemical analysis.

Because the extremely low contents of bioactive compounds in *salvinia* tissues, the *salvinia* extracts demonstrated moderate activities against human tumor cells. Such low activities made *salvinias* ignored in general plant screening for anti-tumor agents.

C. DEFINITIONS

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "sulfonyl" means —S(O)$_2$—; and "sulfinyl" means —S(O)—.

In the context of chemical formulas, the symbol "—" means a single bond, "=" means a double bond; and "≡" means triple bond. The symbol "----" represents an optional bond, which if present is either single or double. The symbol " ==== " represents a single bond or a double bond. Thus, for example, the structure

includes the structures

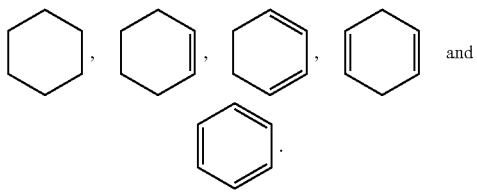

As will be understood by a person of skill in the art, no one such ring atom forms part of more than one double bond. The symbol " ∿∿ ", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀■" means a single bond where the group attached to the thick end of the wedge is "out of the page." The symbol "⦀⦀⦀" means a single bond where the group attached to the thick end of the wedge is "into the page". The symbol "∿∿∿" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

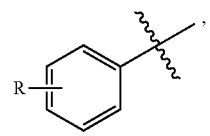

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

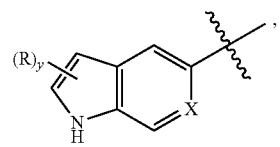

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

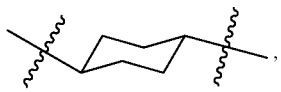 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

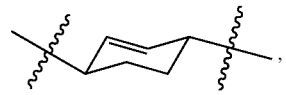 [SMILES: *C1C=CC(*)CC1]

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

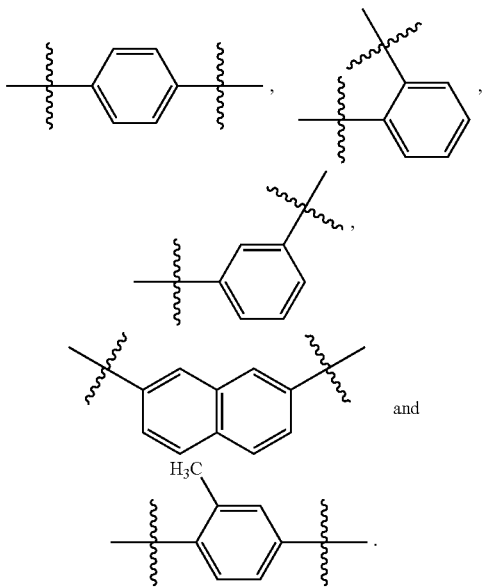

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group-alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolinyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

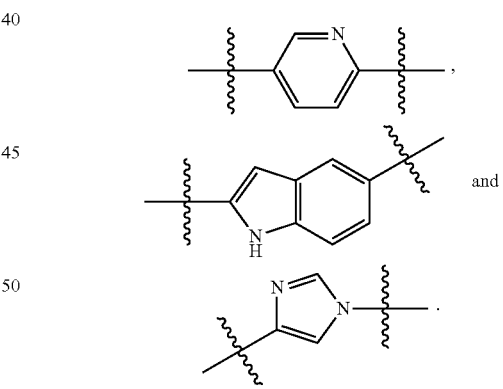

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O) (imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2 n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

Other abbreviations used herein are as follows: $^1$H-NMR is proton nuclear magnetic resonance, AcOH is acetic acid, Ar is argon, $CH_3CN$ is acetonitrile, CHN analysis is carbon/hydrogen/nitrogen elemental analysis, CHNCl analysis is carbon/hydrogen/nitrogen/chlorine elemental analysis, CHNS analysis is carbon/hydrogen/nitrogen/sulfur elemental analysis, DI water is deionized water, DIC is diisopropyl carbodiimide, DMA is N,N-dimethylacetamide, DMAP is 4-(N,N-dimethylamino)pyridine, DMF is N,N-dimethylformamide, EDCl is 1-(3-dimethylaminopropyl)-3-ethylcarbodiimide hydrochloride, EtOAc is ethyl acetate, EtOH is ethanol, FAB MS is fast atom bombardment mass spectroscopy, g is gram(s), h is hour, HOBT is 1-hydroxybenzotriazole hydrate, HPLC is high performance liquid chromatography, IBCF is isobutylchloroformate, KSCN is potassium thiocyanate, L is liter, LiOH is lithium hydroxide, MEM is methoxyethoxymethyl, MEMCl is methoxyethoxymethyl chloride, MeOH is methanol, mg is milligram, $MgSO_4$ is magnesium sulfate, mL is milliliter, mL is milliliter, min is minute, MS is mass spectroscopy, MTBE is methyl tert-butyl ether, $N_2$ is nitrogen, $NaHCO_3$ is sodium bicarbonate, NaOH is sodium hydroxide, $Na_2SO_4$ is sodium sulfate, NMM is N-methylmorpholine, NMP is N-methyl pyrrolidinone, NMR is nuclear magnetic resonance, $P_2O_5$ is phosphorous pentoxide, PTSA is para-toluenesulfonic acid, RPHPLC is reverse phase high performance liquid chromatography, RT is room temperature, TFA is trifluoroacetic acid, THF is tetrahydrofuran, TMS is trimethylsilyl, µg is microgram, and Δ is heating the reaction mixture.

D. PHARMACEUTICAL FORMULATIONS AND ROUTES OF ADMINISTRATION

For administration to a mammal in need of such treatment, the compounds in a therapeutically effective amount are ordinarily combined with one or more excipients appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1,000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range of 750 mg to 90,00 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 µg/kg/body weight, about 5 µg/kg/body weight, about 10 µg/kg/body weight, about 50 µg/kg/body weight, about 100 µg/kg/body weight, about 200 µg/kg/body weight, about 350 µg/kg/body weight, about 500 µg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1,000 mg/kg/body weight or more per administration, and any range derivable therein. In non-limiting examples of a derivable range from the numbers listed herein, a range of about 5 mg/kg/body weight to about 100 mg/kg/body weight, about 5 µg/kg/body weight to about 500 mg/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

E. COMBINATION THERAPY

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines.

F. EXAMPLES

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1

Materials and Methods

General Experimental Procedures

NMR experiments were performed on a JEOL ECS-400 and a Bruker Avance 700 NMR instrument. NMR data were reported as δ (ppm) values and referenced to the solvent used. HRESIMS were acquired on an electrospray instrument (MDS Sciex Pulsar Qstar, Ontario, Canada). Octadecyl-functionalized silica gel, silica gel, Sephadex LH-20, and TLC plates were purchased from Aldrich Chemical Co. HPLC analysis was performed on a Hewlett Packard Series 1100 with a HP 1100 diode array detector using a SB-C18 ODS column (250×4.6 mm, 5 μM, Agilent). Preparative HPLC was performed with an Acuflow Series III pump connected with an Acutect 500 UV/VIS detector using an Econosil ODS column (250×22 mm, 10 μM, Alltech). D-Glucose was purchased from Aldrich.

Collection, Extraction, and Isolation

The whole plants of S. molesta were collected. Air-dried plant material (11.26 kg) was ground to a coarse powder and extracted 48 hrs with 95% EtOH (100 L×2) at room temperature. The combined EtOH extracts were concentrated to give a residue (480 g) under reduced pressure. The residue was then suspended in MeOH/H$_2$O (1,500 mL, 1:1, v/v) and extracted successively with Hexane, EtOA cand n-BuOH. The Hexane and EtOAc extracts exhibited strong cytotoxic activity against A549 cell line with GI$_{50}$ value of 48.61 μg/mL and 54.83 μg/mL, respectively, and thus was subjected to further purification by cytotoxicity directed fractionation against A549 cell line.

The hexane extract (53 g) was applied on a column of silica gel (1,100 g) eluting with the mixture of CH$_2$Cl$_2$/MeOH (50:1, v/v, 5 L). Fractions were monitored by TLC and similar fractions combined to afford 5 fractions, of which fraction 24B and 24C showed the best activity. After being combined, fractions 24B and 24C were further fractionated by ODS column chromatography (1,000 g) eluting with MeOH/H$_2$O (15:85, 30:70, 50:50, and 75:25, v/v, each 3 L), and 1 L of 100% MeOH. According to the HPLC profiles, the eluents were combined to give five subfractions: 25A, 25B, 25C, 25D, and 25E. Fraction 25D afforded eight compounds 7 (2.9 mg), 8 (3.4 mg), 10 (12.9 mg), 11 (2.1 mg), 12 (2.0 mg), 13 (5.7 mg), 43 (3.1 mg), and 44 (5.9 mg), respectively, by preparative HPLC (MeOH/H$_2$O, 80:20, v/v). Fraction 25E afforded eight compounds 6 (2.0 mg), 14 (9.6 mg), 15 (2.0 mg), 16 (2.8 mg), 17 (13.8 mg), 19 (2.4 mg), 20 (2.0 mg), and 21 (2.0 mg), respectively, by preparative HPLC (MeOH/H$_2$O, 82:18, v/v). Compound 18 (1.9 mg) was purified from 25C by preparative HPLC (MeOH/H$_2$O, 99:1, v/v). Compounds 34 (1.0 mg), 35 (1.0 mg), and 22 (10.5 mg) were obtained from 25B by preparative HPLC (MeOH/H$_2$O, 95:5, v/v), respectively. Compounds 33 (17.0 mg), 47 (3.0), and a sub-fraction 25A1 were obtained from 25A by recrystallization in hexane/acetone. Sub-fraction 25A1 was then further isolated by analytical HPLC with 100% MeOH to give compounds 48 (1.2 mg), 49 (1.5 mg), and 50 (1.0 mg).

The EtOAc-soluble extract (83.9 g) was applied to a column of Diaion HP-20 eluting with H$_2$O, MeOH—H$_2$O (30:70, 45:55, 60:40, and 80:20), and MeOH to give five fractions: F30 (30% methanol elution, 25 g), F45 (45% methanol elution, 13 g), F60 (60% methanol elution, 13.6 g), F80 (80% methanol elution, 7.8 g), and F100 (methanol elution, 7.8 g). These fractions were evaluated for cytotoxicity against A549 cell line, of these, fraction F45 and F60 showed the most potent inhibition of cancer cell proliferation. Faction F60 was separated by silica gel column chromatography (500 g) eluted with a CH$_2$Cl$_2$/MeOH gradient (7:1, 3:2, 2:3, and 1:99, v/v, each 3 L) to afford compounds 45 (5.0 mg) and 46 (23 mg). The rest 47 fractions were combined into fractions FI6-FVI6. After being combined, FI6 and FII6 were separated by preparative HPLC to give compounds 9 (8.0 mg), 24 (1.3 mg), 25 (1.2 mg) and 26 (1.8 mg) eluted with CH$_3$CN/0.5% HOAc in H$_2$O (54:46, v/v). Fraction FIV6 was applied to a ODS column eluting with MeOH/H$_2$O (1:1, v/v) to afford six sub-fractions: FV6a-FV6f. Compounds 23 (3.0 mg), 27 (22 mg), 30 (2.3 mg), and 32 (1.0 mg) were purified by preparative HPLC from fraction FV6c (MeOH/H$_2$O, 54:46, v/v). HPLC isolation of FV6f eluted with MeOH/H$_2$O (35:65, v/v) gave compounds 4 (600 mg) and 5 (10.9 mg). After being combined, fractions FV6 and FVI6 were further fractionated by HPLC eluting with MeOH/H$_2$O (30:70) to give compounds 1 (2.2 mg) and 28 (1.0 mg). Faction F45 was separated by silica gel column chromatography (500 g) eluted with a gradient CH$_2$Cl$_2$/MeOH (10:1, 5:1, 3:2, and 2:3, v/v, each 3 L) and 1 L of MeOH, to give five fractions FI4-FV4. Compounds 29 (1.2 mg) and 31 (1.1 mg) were purified by preparative HPLC from fraction FIV4 by preparative HPLC (MeOH/H$_2$O, 30:70, v/v). Faction F80 (7.8 g) was separated by silica gel column chromatography eluted with a CH$_2$Cl$_2$/MeOH gradient (15:1, 10:1, 5:1, 2:1 and 0:1, v/v, each 1.5 L) to afford 6 fractions F8a-F8f. F8b was subjected to an ODS column, eluted with a gradient of MeOH/H$_2$O (from 40:60 to 90:10), to give three subfractions, F8b1-F8b3. F8b1 was subjected to a silica gel column, eluted with a gradient of hexane/acetone (from 10:1 to 2:1), to yield compounds 2 (6 mg), 41 (5.2 mg), and 42 (1.9 mg). F8b2 was subjected to a silica gel column, eluted with a gradient of hexane/EtOAc (from 4:1 to 0:1), to give three fractions F8b2a-F8b2c. Compounds 36 (4.2 mg), 39 (7 mg), and 40 (9 mg) were purified by preparative HPLC from fraction F8b2b by preparative HPLC (MeOH/H$_2$O, 70:30, v/v). F8c was subjected to a silica gel column, eluted with a gradient of hexane/acetone (from 10:1 to 2:1), to yield compounds 3 (6 mg), 37 (5.2 mg), and 38 (9 mg).

Hydrolysis and Determination of Absolute Configuration of Sugar

Compound 4 (10.0 mg) and 5 (5.0 mg), respectively, was refluxed with 2 mL of 5% H$_2$SO4 at 80° C. for 3 h (Toyota, 2002). After cooling, the reaction mixture was diluted with water, and then partitioned three times with EtOAc (each 5 mL). The remaining aqueous solution was evaporated to dryness with nitrogen gas stream. Compound 1 (1.0 mg) was incubated in 400 µL 1 M HCl in dioxane/water (1:1, v/v) at 80° C. for 3 h. The solution was evaporated to dryness by blowing nitrogen gas. The residue was suspended in 200 µL water and partitioned three times with EtOAc (400 µL×3). The remaining aqueous solution was evaporated to dryness with nitrogen gas stream.

The absolute configuration of sugar in each residue was determined by a method described by Tanaka et al with minor modifications (Tanaka, 2007). Briefly, the sample was dissolved in 200 µL pyridine containing L-cysteine methyl ester hydrochloride (equivalent to the theoretical weight of sugar in the sample) and incubated at 60° C. After 1 hr incubation, 200 µL o-torylisothiocyanate (equivalent to the theoretical weight of sugar in the sample) pyridine solution was added into the mixture and incubated at 60° C. for one additional hour. The reaction mixture was directly analyzed by HPLC (Agilent 1100 HPLC system, Poroshell 120 EC-C18, 4.6×50 mm, 2.7 µm, 0.5 mL/min, 250 nm, 22% acetonitrile in 50 mM H$_3$PO$_4$, then washing column with 90% acetonitrile in 50 mM H$_3$PO$_4$). By HPLC analysis, the retention time of the product from the standard sugar was found at 15.7 min for D-glucose. By comparison of the retention time with the standard and co-HPLC, the absolute configuration of sugar in the hydrolysis was identified.

Cytotoxicity Assays

Human exocrine pancreatic cancer (PANC-1 and BxPC-3), non-small cell lung cancer (A549), prostate cancer (PC-3), breast cancer (MDA-MB-231), and leukemia (HL-60) were obtained from The University of Texas M. D. Anderson Cancer Center, Houston, Tex., and Normal human lung fibroblasts cells (MRC-5) was purchased from the American Type Culture Collection (ATCC). PC-3, A549 and HL-60 cells were maintained in RPMI 1640 medium supplemented with 10% (v/v) fetal bovine serum and antibiotics (1,000 units/mL penicillin-streptomycin solution, Hyclone). PANC-1 and MRC-5 was cultured in complete growth medium according to the ATCC protocols. Cells were grown at 37° C. and 5% CO2 in humidified air.

Cytotoxicity of total extracts of *S. molesta* was tested against PANC-1, A549, PC-3, and MRC-5. Cytotoxicity of the fractions was determined using A549 cells, a human non-small lung cancer cell line. Fractions were tested at 25, 50, and 100 µg/mL. The isolated pure compounds were tested in each of the cultured human tumor and normal cell lines at various concentrations between 1 and 100 µM with three replications. Human tumor and normal cells were inoculated into 96 well microtiter plates in 90 µL at plating densities ranging from 5,000 to 40,000 cells/well (measured by Z2 Coulter Counter of Beckman) depending on the doubling time of individual cell lines. Cell growth and viability was measured by WST-8 (Water Soluble Tetrazolium) assays following a standard protocol (Cell Counting Kit-8, Dojindo Molecular, Maryland). The WST-8 assay measured the relative activity of mitochondrial reductase enzymes in viable cells. A control WST reading ($T_0$) before treatment was measured, then cells were continuously exposed to isolates for 48 h. After WST added and incubated for 2 h, the amount of formazan was measured by using a microplate spectrophotometer (µQuant spectrophotometer, Bio-Tek Instruments, Inc., Vermont) at 450 nm. $T_C$ or $T_D$ represents the readings of the untreated control or with tested compounds. Percent cell-growth (G) and percent cell-growth inhibition (GI) was calculated as: $G=(T_D-T_0/T_C-T_0)\times100$; $GI=[1-(T_D-T_0/T_C-T_0)]\times100$ for which $T_D \geq T_0$; and $G=(T_D-T_0/T_0)\times100$; $GI=[1-(T_D-T_0/T_0)]\times100$ for which $T_D<T_0$. To determine the inhibitory potency of active compounds ($GI_{50}$, 50% cell-growth inhibition), tests were extended to additional concentrations (varying from 0.01 to 100 µM). Cancer drug doxorubicin was used as the positive controls in the cell-based assays.

Cell Proliferation Assays

CCK-8 (Dojindo Molecular, Maryland) was used to measure the proliferation response of salviniol (6) and montbretol (8) against human exocrine pancreatic cancer cell lines (PANC-1 and BxPC-3), according to the manufacturer's instructions. Cell were grown in growth medium plus 10% FBS and 5% antibiotics in 96-well plates and then were treated with various concentrations of test compounds and incubated for 12, 24, 48, and 72 h, respectively. The end of the incubation period, 10% CCK-8 solution was added to the wells. After 2 h incubation, the absorbance at 450 nm was measured. A calibration curve was prepared using the absorbance observed known numbers of viable cells.

Example 2

The EtOH extract of *S. molesta* was found to exhibit moderate selective cytotoxicity against several human cancer cell lines (A549: $GI_{50}$ 84.34 µg/mL; PC-3: $GI_{50}$ 100 µg/mL; PANC-1: $GI_{50}$ 69.92 µg/mL), but no activity for normal lung cell line (MRC-5: $GI_{50}$>100 µg/mL). This prompted the inventors to phytochemically examine the chemical constituents responsible for the cytotoxic activity using bioactivity-guided fractionation (FIG. 1). This paper reports the isolation, structural elucidation, and cytotoxic activity of six new compounds, 10(S)-hydroxy-2,6,10-trimethyl-2E,6E,11-dodecatrienoic acid 10-O-β-D-glucopyranoside (1), salvinin A (2), salvinin B (3), salviniside I (4), salviniside II (5), and salviniol (7-(menth-1-en-4-ol)-ferruginol) (6) together with 16 abietane diterpenes: 14-deoxycoleon U (7) (Kusumoto, 2009; Fraga, 2005), montbretol (8) (Ayhan, 1992), 5,6-dehydrosugiol (9) (Xu, 2011), 7-methoxyrosmanol (10) (Guerrero, 2006), montbretyl 12-methyl ether (11) (Ulubelen, 1992), 11-hydroxysugiol (12) (Xiang, 2002), sugiol (13) (Benjamin, 2003), ferruginol (14) (Tezuka, 1998), 7-hydroxyferruginol (15) (Kuo, 2002), 6,7-dehydroferruginol (16) (Kuo, 1998), 12-hydroxy simonellite (17) (Elisa, 1969), simonellite (18) (Elisa, 1969), 1-oxomiltirone (19) (Sairafianpour, 2001), royleanone (20) (Tezuka, 1998), 6,7-dehydroroyleanone (21) (Kusumoto, 2009), 12-hydroxy-6,7-secoabieta-8,11,13-triene-6,7-dial (22) (Fang, 1986) and 28 other known compounds: 10(S)-hydroxy-2,6,10-trimethyl-2E,6E,11-dodecatrienoic acid (23) (Miyazawa, 1996), 6-hydroxy-7E,9Z-pentadecadienoic acid (24) (Tamura, 2010), 11-hydroxy-7Z,9E,13E-hexadecatrienoic acid (25) (Xiang, 2008), 13-hydroxy-9Z,11E,15E-octadecatrienoic acid (26) (Bang, 2002), 4-hydroxy methyl benzoate (27), 3,4-dihydroxy benzoic acid (28), 4-hydroxy benzoic acid (29), p-hydroxybenzaldehyde (30) (Avupati, 2012), cucurbic acid (31) (Fujita, 1996), cucurbinoyl-isoleucine (32) (Hans-Dieter, 1995), hop-22

Figure 2:
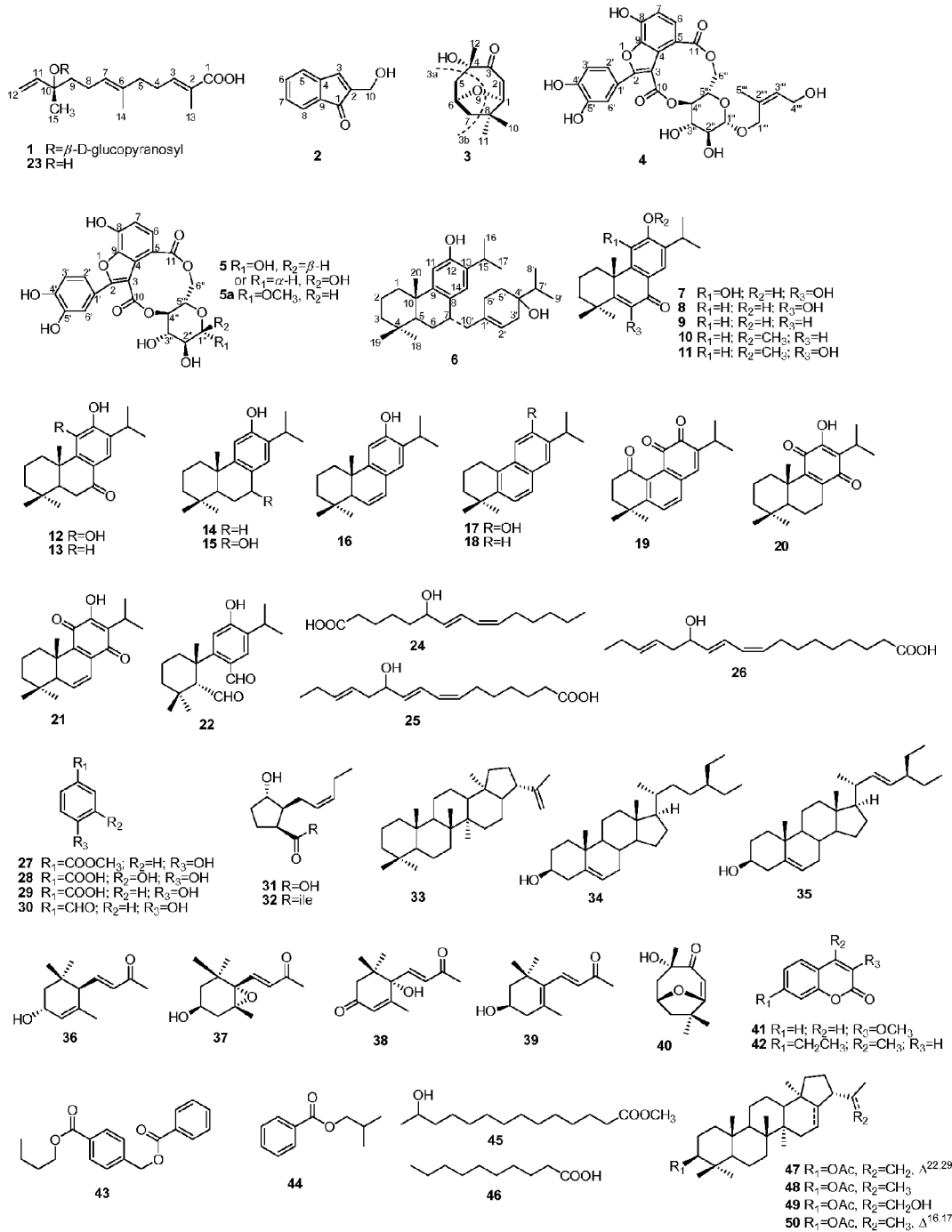
FIG. 2. Structures of the compounds isolated from *Salvinia molesta*.
Figure 3A:
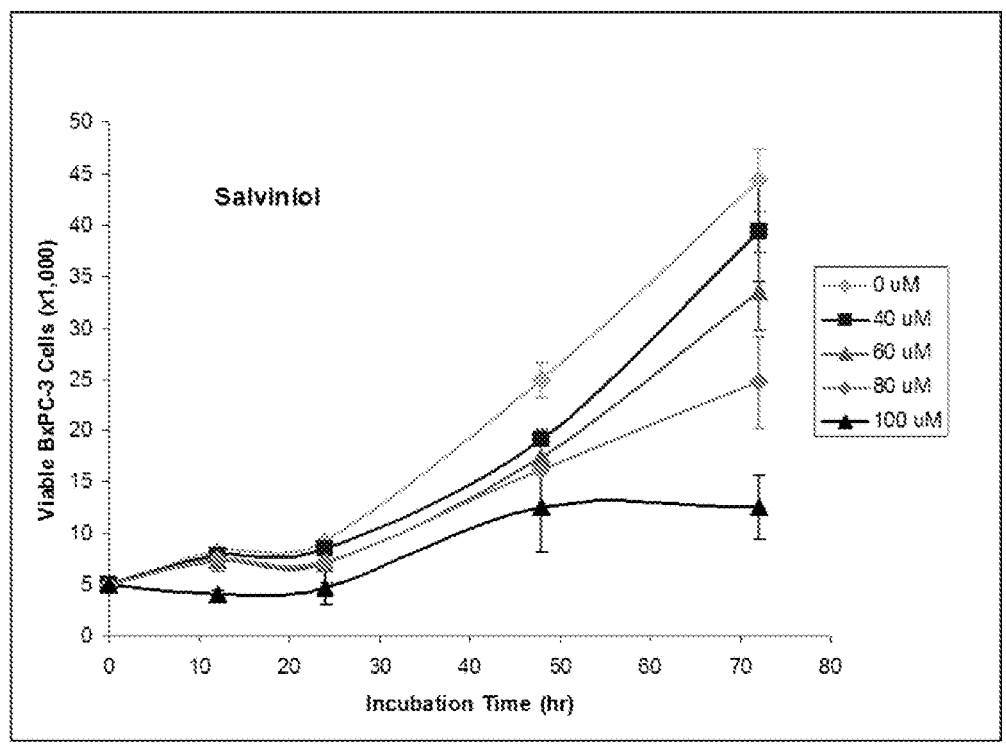
FIGS. 3A-D.
Figure 3B:
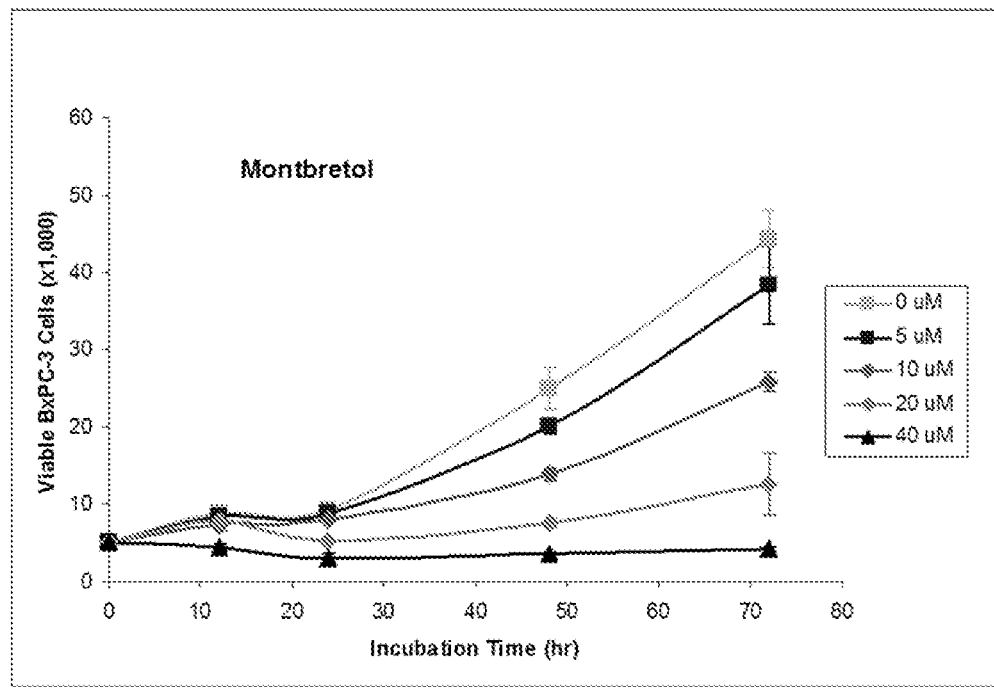
Figure 3C:
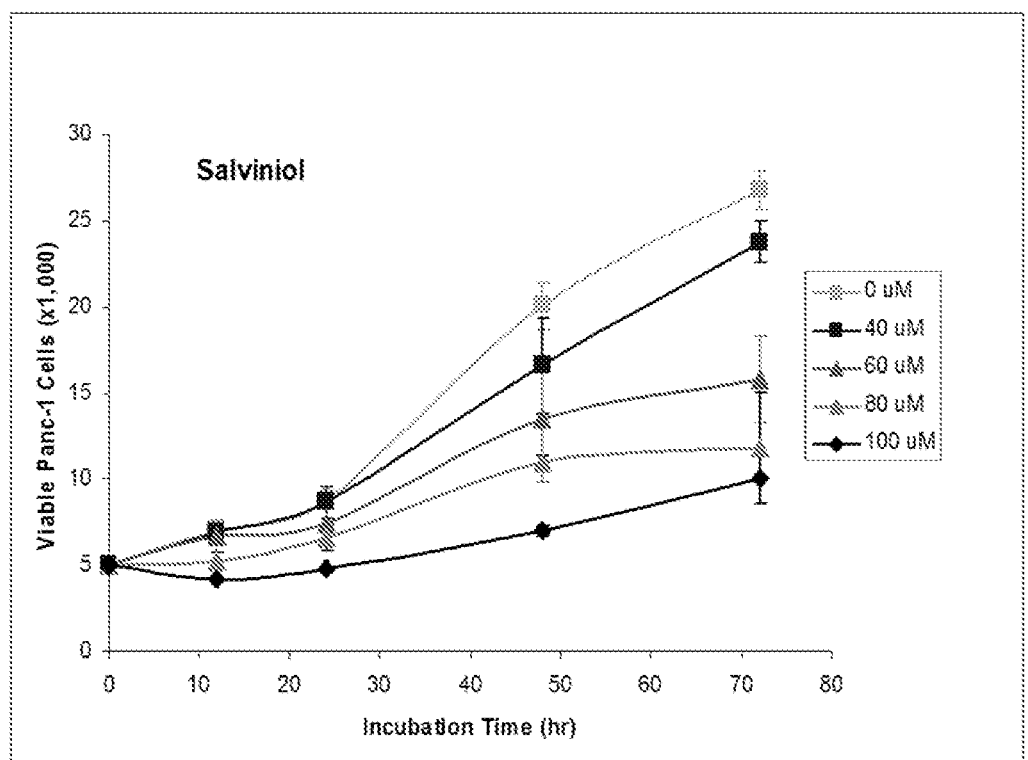
Figure 3D:
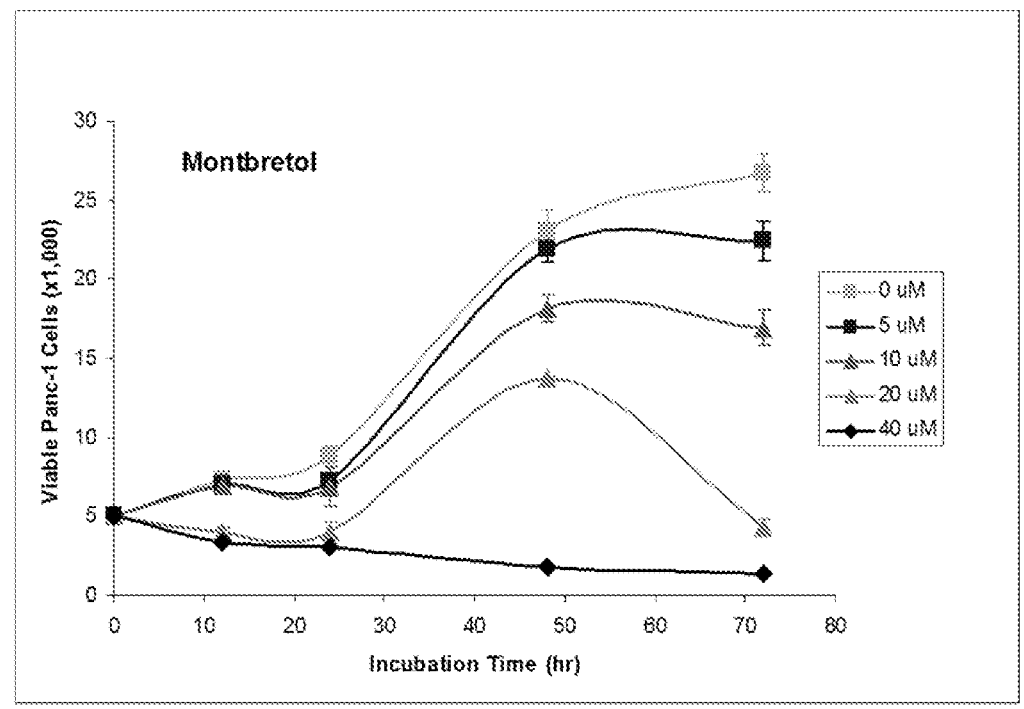

(29)-ene (33) (Mahato, 1994), β-sitosterol (34), β-stigmasterol (35), (3R,6R,7E)-3-hydroxy-4,7-megastigmadien-9-one (36) (DellaGreca, 2004), annuionone D (37) (Zhao, 2011), dehydrovomifoliol (38) (Tan, 2012), (+)-3-hydroxy-β-ionone (39) (DellaGreca, 2004), pubinernoid A (40) (Huang, 2006), 3-methoxycoumarin (41) (Mustafa, 1963), 4-methyl-7-ethyl-coumarin (42) (Brubaker, 1986), asiaticin (43) (Siddiuui, 2007), 2-(benzoyloxy)-1,1-dimethyl-ethyl (44) (Fielding, 2002), 13-hydroxy-tetradecanoic acid methyl ester (45), decanoic acid (46) (Yu, 1999), 3β-acetoxy-20 (29)-hopene (47), 3β-acetoxy-hopane (48), 3β-acetoxy-29-hydroxy-hopane (49), 3β-acetoxy-16-hopene (50) (FIG. 2). The identities of these known compounds were determined by analyzing their spectroscopic data and confirmed by comparing their values with those in the literature.

Compound 1 was isolated as a pale, amorphous powder. The molecular formula $C_{21}H_{33}O_8$ was deduced from the [M-H]$^+$ peak at m/z 413.2174 (calcd for 413.2175) in the HR-ESI-MS. The $^{13}C$ NMR spectrum of 1 displayed 21 carbon signals, of which 15 were assigned to the aglycone, including 4 quaternary carbons [one carbonyl (δ 171.12), two olefinic quaternary carbon (δ 134.29 and 127.93), and one oxyquaternary carbons (δ 80.50)], and the remaining 6 to the sugar moiety (Table 2).

TABLE 2

$^{13}C$ and $^1H$ NMR data of compound 1 (in MeOH-d$_4$)$^a$

| Position | $\delta_C$ (ppm) | $\delta_H$ (ppm) |
|---|---|---|
| 1 | 171.12 | |
| 2 | 127.93 | |
| 3 | 142.19 | 6.68 (1H, t, J = 6.67 Hz) |
| 4 | 26.87 | 2.26 (1H, dd, J = 7.33 and 7.99 Hz) |
| 5 | 37.93 | 2.09 (1H, t, J = 7.33 Hz) |
| 6 | 134.29 | |
| 7 | 125.13 | 5.14 (1H, t, J = 7.79 Hz) |
| 8 | 22.21 | 2.06 (1H, m) |
| 9 | 41.13 | 1.56 (1H, m) |
| 10 | 80.50 | |
| 11 | 143.09 | 5.90 (1H, dd, J = 10.99 and 17.40 Hz) |
| 12 | 114.14 | 5.18 (1H, dd, J = 17.40 and 1.37 Hz) |
|   |        | 5.00 (1H, dd, J = 10.99 and 1.37 Hz) |
| 13 | 11.14 | 1.77 (3H, s) |
| 14 | 14.52 | 1.59 (3H, s) |
| 15 | 21.93 | 1.35 (3H, s) |
| Glc-1' | 98.18 | 4.31 (1H, d, J = 7.79 Hz) |
| Glc-2' | 73.75 | 3.13 (1H, m) |
| Glc-3' | 76.60 | 3.12 (1H, m) |
| Glc-4' | 70.29 | 3.25 (1H, t, J = 8.70 Hz) |
| Glc-5' | 76.34 | 3.28 (1H, m) |
| Glc-6' | 61.40 | 3.61 (1H, dd, J = 5.50, 11.91 Hz) |
|   |        | 3.78 (1H, dd, J = 2.37, 11.91 Hz) |

$^a$The assignment was based upon COSY, HSQC, and HMBC experiments.

An anomeric carbons (δ 98.18) and an anomeric protons at δ 4.31 (1H, d, J=7.79 Hz) observed in the HSQC spectrum, in addition to signals of four oxymethine groups and an oxymethylene group at δ 73.75 (CH, C-2'), 76.60 (CH, C-3'), 70.29 (CH, C-4'), 76.34 (CH, C-5'), and 61.40 (CH2, C-6') suggested the sugar as β-glucopyranose (Zhang, 2008), which was further determined to be β-D-glucopyranose by co-HPLC analysis with authentic sugar after acid hydrolysis of compound 1 (Tanaka, 2007). In the $^1H$ NMR spectrum, signals for three methyls appearing as singlet peaks [$\delta_H$ 1.35, 1.59, 1.77], four methylene, two olefinic methines [$\delta_H$ 6.68 (1H, t, J=6.67 Hz), 5.14 (1H, t, J=7.79 Hz)], and a terminal vinyl group having a small geminal coupling (J=1.37 Hz), a trans vicinal coupling (J=17.40 Hz), and a cis vicinal coupling (J=10.99 Hz) indicated the presence of a sesquiterpene moiety. Its structural fragment was determined by 2D NMR data, including COSY, HSQC, and HMBC experiments. From the COSY spectrum of compound 1, it was possible to establish the proton sequence from H-3 to H$_2$-5 through H$_2$-4; H-7 to H$_2$-9 through H$_2$-8; and H-11 to H$_2$-12. The methyl groups attached at C-2, C-6, and C-10 were determined on the basis of the key HMBC correlations from H$_3$-13 to C-1, C-2, and C-3; H$_3$-14 to C-5, C-6, and C-7; and H$_3$-15 to C-9, C-10, and C-11. The above HMBC correlations also confirmed the linkages established by the COSY experiment. The NMR data comparison of compounds 1 and 23 concluded that compound23 was the aglycone of compound 1 identified as 10(S)-hydroxy-2,6,10-trimethyl-2,6,11-dodecatrienoic acid (Miyazawa, 1996). The long-range correlation of $\delta_H$ 4.31 (Glc H-1) of the glucose (Glc) with $\delta_C$ 80.50 (C-10) of the skeleton from HMBC correlations suggested that Glc was located at C-10 position. The E- and E-geometry of the two double bonds at C-2 and C-6 were identified by the NOESY correlations between H-13/H-4 and H-5, H3-14 and H-8. The structure of compound 1 was formulated as 10(S)-hydroxy-2,6,10-trimethyl-2E,6E,11-dodecatrienoic acid 10-O-β-D-glucopyranoside.

Salvinin A (2), obtained as a pale yellow powder. The molecular formula $C_{10}H_8O_2$ was established by HR-EI-MS and 1 D NMR spectrum (Table 3).

TABLE 3

$^{13}C$ and $^1H$ NMR data of compound 2$^a$

| Position | $\delta_C$ (ppm) | $\delta_H$ (ppm) |
|---|---|---|
| 1 | 195.6 | |
| 2 | 126.1 | |
| 3 | 132.6 | 8.17, s |
| 4 | 136.5 | |
| 5 | 121.3 | 8.19 (1H, dd, J = 8.4, 2.4 Hz) |
| 6 | 121.9 | 7.20, m |
| 7 | 123.0 | 7.20, m |
| 8 | 110.6 | 7.42 (1H dd, J = 7.6, 2.2 Hz) |
| 9 | 113.6 | |
| 10 | 64.9 | 4.73, s |

$^a$The assignment was based upon COSY, HSQC, and HMBC experiments.

The $^1H$-NMR spectrum of compound 2 displayed the signals of five sp2 protons and two sp3 protons. The $^{13}C$-NMR spectrum with DEPT experiments displayed 10 carbon resonances comprising one oxygenated methylene, five sp2 methines, and four quaternary carbons (one keto group). The $^1H$-NMR spectrum (δ 8.19, dd, J=8.4 and 2.4 Hz, H-5; δ 7.20, m, H-6 and H-7; δ 7.42, dd, J=7.6 and 2.2 Hz, H-8) revealed an o-disubstituted benzene ring substructure. HMBC correlations of H$_2$-10 to C-1, C-2 and C-3, indicated that the only oxygenated methylene (C-10) was placed at C-2. Thus, compound 2 was elucidated as 2-hydroxymethyl, Indone.

Salvinin B (3), obtained as an amorphous powder. The molecular formula was established as $C_{11}H_{16}O_2$ by HR-ESI-MS and 1 D NMR spectrum. The $^1H$-NMR spectrum (Table 4) showed three methyls at δ 1.25, 1.29, and 1.57 as singlets, and one trisubstituted double bond at δ 5.75. The $^{13}C$-NMR spectrum (Table 4) showed 11 carbon signals, identified by a DEPT experiment as three methyls, two methylenes, one oxymethine, one double bond carbon, two quaternary carbons and one carbonyl carbon.

TABLE 4

$^{13}C$ and $^1H$ NMR data of compound 3$^a$

| Position | $\delta_C$ (ppm) | $\delta_H$ (ppm) |
|---|---|---|
| 1 | 172.6 | |
| 2 | 112.4 | 5.75, s |
| 3 | 182.6 | |
| 4 | 87.2 | |
| 5 | 47.6 | 2.45, dt, J = 12.4, 5.2 Hz; 1.41, m |
| 6 | 63.9 | 4.07, m |
| 7 | 47.9 | 1.97 dt, J = 12.4, 2.8 Hz; 1.36, m |
| 8 | 34.8 | |
| 10 | 29.0 | 1.25, s |
| 11 | 24.0 | 1.29, s |
| 12 | 24.4 | 1.57, s |

$^a$The assignment was based upon COSY, HSQC, and HMBC experiments.

The $^1H$—$^1H$ COSY spectrum together with the HSQC data revealed a —$CH_2$—CH—$CH_2$— unit in bold (3a). HMBC correlations of $H_3$-12/C-3 and C-4, H-2/C-1, C-3, C-4 and C-8, $H_3$-11/C-1, C-8 and C-10 suggested the partial structure 3b (FIG. 2). The two substructures were linked via C-4 and C-5, C-7 and C-8 by the HMBC correlations of $H_3$-11/C-7 and $H_3$-12/C-5, respectively. The only leftover uncertainty for the planar structure of 3 was the remaining one degree of unsaturation, which required the presence of an additional ring. The relatively upfield shifted of the $^{13}C$ NMR data at C-1 at δ 172.6 and the relatively downfield shifted of C-6 at δ 63.9, suggesting that an ether bridge was present between C-1 and C-6 to form an oxygen ring. The relative stereochemistry of compound 3 was established on the basis of the ROESY experiment. The strong ROESY correlations of H-5β/$H_3$-12 and H-6β indicated that H-6, and Me-12 were β-oriented. The other configurations were established as the same as compound pubinernoid A (40) by comparing their spectroscopic data (Huang, 2006). The gross structure of compound 3 was thus established as (4S*,6S*)-4-hydroxy-4,8,8-trimethyl-9-oxabicyclo[4.2.1]non-1-en-3-one.

Compound 4 was obtained as colourless powder and was assigned a molecular formula of $C_{27}H_{26}O_{13}$, as deduced from the [M-H]$^1$ peak at m/z 557.1297 (calcd for 557.1295) in the HR-ESI-MS. The $^{13}C$ and $^1H$-NMR spectrum of compound 4 (Table 5) displayed a set of glycoside signals ($\delta_C$ 103.7, 77.7, 75.6, 74.5, 68.7, 65.7). The anomeric proton at δ 4.39 with coupling constant $J_{H1,2}$ value (d, J=7.8 Hz) demonstrated the presence of a β-glucopyranosyl moiety (Narasimhulua, 2010). The monosaccharide was further determined to be D configuration after chemical degradation of compound 4 (Oiso, 2001; Toyota, 2002) and HPLC analysis with authentic sugar. The $^1H$-NMR spectrum of compound 4 contained signals due to two oxygenated methylenes at δ 4.11 (2H, d, J=6.4 Hz, H-4''') and 4.06, 4.21 (1H each, d, J=12.2 Hz, H-1'''), a vinyl methyl group and an olefinic proton at δ 1.70 (3H, s, H-5''') and 5.65 (1H, dd, H-3'''). Thus, compound 4 possessed a hemiterpene with a trisubstiued double bond (Ding, 1999; Kazuko, 2006). Five aromatic protons were also found in the $^1H$-NMR spectrum (Table 5), of which three signals at δ 7.39 (1H, dd, J=1.8 and 8.2 Hz, H-2'), δ 6.83 (1H, d, J=8.2 Hz, H-3'), and 7.45 (1H, d, J=1.8 Hz, H-6') were characteristic of a 1,2,4-trisubstituted phenyl moiety, the remaining two at δ 7.67 (1H, d, J=8.2 Hz, H-6) and 6.79 (1H, d, J=8.2 Hz, H-7) were assigned to a 1,2,3,4-tetra substituted phenyl group (Narasimhulua, 2010).

TABLE 5

$^1H$ and $^{13}C$-NMR Data (δ) of Compounds 4 and 5$^a$

| | 4 | | 5 β-anomer | | 5 α-anomer | |
|---|---|---|---|---|---|---|
| Position | $\delta_C$ | $\delta_H$ | $\delta_C$ | $\delta_H$ | $\delta_C$ | $\delta_H$ |
| 2 | 158.4 | | 158.3 | | 158.4 | |
| 3 | 110.2 | | 110.3 | | 110.2 | |
| 4 | 129.7 | | 129.7 | | 129.7 | |
| 5 | 114.8 | | 114.9 | | 114.8 | |
| 6 | 130.0 | 7.67 (1H, d, J = 8.2 Hz) | 130.0 | 7.70 (1H, d, J = 8.2 Hz) | 130.0 | 7.70 (1H, d, J = 8.2 Hz) |
| 7 | 112.1 | 6.79 (1H, d, J = 8.2 Hz) | 112.1 | 6.82 (1H, d, J = 8.2 Hz) | 112.1 | 6.82 (1H, d, J = 8.2 Hz) |
| 8 | 149.0 | | 148.8 | | 148.8 | |
| 9 | 143.5 | | 143.5 | | 143.5 | |
| 10 | 168.5 | | 168.7 | | 168.7 | |
| 11 | 168.0 | | 168.1 | | 168.1 | |
| 1' | 121.6 | | 121.6 | | 121.6 | |
| 2' | 121.4 | 7.39 (1H, dd, J = 8.2 and 1.8 Hz) | 121.5 | 7.39 (1H, dd, J = 8.5 and 1.8 Hz) | 121.4 | 7.39 (1H, dd, J = 8.5 and 1.8 Hz) |
| 3' | 116.7 | 6.83 (1H, d, J = 8.2 Hz) | 116.8 | 6.84 (1H, d, J = 8.5 Hz) | 116.8 | 6.84 (1H, d, J = 8.5 Hz) |
| 4' | 149.4 | | 149.4 | | 149.4 | |
| 5' | 146.8 | | 146.8 | | 146.8 | |
| 6' | 115.7 | 7.45 (1H, d, J = 1.8 Hz) | 115.7 | 7.45 (1H, d, J = 1.8 Hz) | 115.7 | 7.45 (1H, d, J = 1.8 Hz) |
| Glc-1" | 103.7 | 4.39 (1H, d, J = 7.8 Hz) | 98.6 | 4.57 (1H, d, J = 7.8 Hz) | 94.4 | 5.14 (1H, d, J = 3.7 Hz) |
| Glc-2" | 75.6 | 3.32 (1H, dd J = 8.2 and 8.7 Hz) | 76.7 | 3.27 (1H, dd, J = 7.8 and 9.2 Hz) | 74.2 | 3.51(1H, dd, J = 3.7 and 9.2 Hz) |
| Glc-3" | 74.5 | 3.59 (1H, dd, J = 9.6 and 9.2 Hz) | 74.5 | 3.57 (1H, dd, J = 9.6 and 9.2 Hz) | 71.6 | 3.83 (1H, t, J = 10.1 Hz) |
| Glc-4" | 77.7 | 5.27 (1H, t, J = 9.6 Hz) | 77.8 | 5.30(1H, t, J = 9.6 Hz) | 78.4 | 5.24 (1H, t, J = 9.6 Hz) |
| Glc-5" | 68.7 | 3.77 (1H, td, J = 10.1 and 4.1 Hz) | 68.9 | 3.78 (1H, td, J = 10.5 and 4.1 Hz) | 64.4 | 4.24 (1H, td, J = 10.5 and 4.1 Hz) |
| Glc-6" | 65.7 | 3.93 (1H, t, J = 10.5 Hz) 5.02 (1H, dd, J = 10.5 and 4.1 Hz) | 65.8 | 3.94 (1H, t, J = 11.0 Hz) 5.04 (1H, dd, J = 10.3 and 4.1 Hz) | 66.4 | 3.91 (1H, t, J = 11.0 Hz) 4.97(1H, dd, J = 10.3 and 4.1 Hz) |

TABLE 5-continued

¹H and ¹³C-NMR Data (δ) of Compounds 4 and 5[a]

| | 4 | | 5 | | | |
|---|---|---|---|---|---|---|
| | | | β-anomer | | α-anomer | |
| Position | $\delta_C$ | $\delta_H$ | $\delta_C$ | $\delta_H$ | $\delta_C$ | $\delta_H$ |
| 1''' | 75.8 | 4.06 (1H, d, J = 12.2 Hz); 4.21 (1H, d, J = 12.2 Hz) | | | | |
| 2''' | 135.8 | | | | | |
| 3''' | 128.5 | 5.65 (1H, dd, J = 5.9 and 6.4 Hz) | | | | |
| 4''' | 59.2 | 4.11 (2H, d, J = 6.4 Hz) | | | | |
| 5''' | 14.2 | 1.70 (3H, s) | | | | |

[a]The assignment was based upon COSY, HSQC, and HMBC experiments.

A close inspection of the ¹³C-NMR spectrum of compound 4, together with the MS data, clearly revealed that the 1,2,3,4-tetrasubstituted phenyl moiety should be a part of a 8-carbon benzofuran skeleton (Hsieh, 2006; Kazuko & Kentaro, 2006). In additional, the ¹³C NMR spectra of compound 4 displayed two ester carbonyl carbons at δ 168.0 and δ 168.5. As observed in the HMBC spectrum of compound 4, three key HMBC correlation among $\delta_H$ 4.39 (glc H-1'') and $\delta_C$ 75.8 (hemiterpene C-1''') established that the glucose was attached to the assigned position; H-6 at $\delta_H$ 7.67 and Glc H-6'' at $\delta_H$ 3.93 with a carbonyl carbon at $\delta_C$ 168.0 (C-11) established the linkage between the benzofuran unit and H-6'' of Glc. Similarly, the other ester carbonyl carbon ($\delta_C$ 168.5, C-10) was attached to H-4'' of Glc position by the HMBC spectrum analysis. These long-range HMBC correlations of H-2' to C-1', C-6' and C-2, and of H-6' to C-1', C-2' and C-2 established the connectivity of the benzofuran skeleton with 1,2,4-trisubstituted phenyl moiety. The 1,1-ADEQUATE spectrum also confirmed the assignment. The relatively downfield shift of C-3 at δ 110.2 and the remaining one degree of unsaturation established the linkage of the C-3 and C-10. The complete assignment of the protons and carbons was achieved by a combination of ¹H, ¹³C, HSQC, ¹H—¹H COSY, HMBC and 1,1-ADEQUATE spectral analyses. Moreover, NOEs were observed between the methylene protons at C-1''' and C-4''', indicating the E-configuration of the hemiterpene moiety. The structure of compound 4 was identified as 1''-O-[(E)-2'''-methyl-but-2'''-en-4'''-ol]-4'',6''-O-[3,5-dicarbonyl-8-hydroxy-2-(4',5'-dihydroxy-phenyl)-1-benzofuran-2-yl]-β-D-glucopyranose and was named salviniside I.

Compound 5 were, isolated by HPLC, obtained as colorless powders and showed an [M-1]⁺ at m/z 473.0714 (calcd for 473.0720) in the HR-ESI-MS, suggesting the molecular formula to be $C_{22}H_{18}O_{12}$. The NMR spectroscopic data of 5 (Table 5), was different from those of compound 4 mainly in the absence of the signals for the hemiterpene moiety, which was attached at the C-1 position of the glucose. Instead, compound 5 displayed similarly two set of glycoside signals (Table 5) with two anomeric proton at δ 4.57 (1H, d, J=7.8 Hz, β-H-1'') and δ 5.14 (1H, d, J=3.7 Hz, α-H-1''), and two protonated carbon at $\delta_{C\text{-}\beta}$ 98.6 and $\delta_{C\text{-}\alpha}$ 94.4 observed in the HSQC spectrum. Acid hydrolysis of compound 5 liberated D-glucose identified by co-HPLC with authentic sugar (Oiso, 2001; Toyota, 2002). The analysis of the COSY, HSQC spectra indicated compound 5 is an isomeric mixture of α and β-D-glucopyranosides (Choudhary, 2008; Narasimhulua, 2010; Ding, 1999). This conclusion was confirmed by production of compound 5a with β-anomeric methyl glucose upon methylation of compound 5 with MeOH in 10% $H_2SO_4$. In the NMR spectrum, each signals of the aglycon part of compound 5 appeared essentially in duplicate owing to the formation of a mixture of α and β-anomers. The complete assignment of the protons and carbons was achieved by a combination of ¹H, ¹³C, HSQC, ¹H—¹H COSY and HMBC spectral analyses. Thus, compound 5 was identified as 4'',6''-O-[3,5-dicarbonyl-8-hydroxy-2-(4',5'-dihydroxy-phenyl)-1-benzofuran-2-yl]-α/β-D-glucopyranose and named salviniside II.

Compound 6 was isolated as a colorless powder. The molecular formula $C_{30}H_{46}O_2$ was deduced from the [M-H]⁺ peak in the HR-ESI-MS, suggesting the presence of eight degrees of unsaturation. The ¹³C-NMR spectrum indicated the presence of four double bonds [$\delta_C$ 150.9 (s), 148.8 (s), 136.4 (s), 131.6 (s), 127.1 (d), 120.9 (d), 110.8 (d)] and an oxygenated carbon [$\delta_C$ 72.1 (s)]. Its ¹HNMR spectrum had signals for three tertiary methyl groups ($\delta_H$ 0.87, 0.89, 1.12), two isopropyl groups [$\delta_H$ 0.93, 0.95, 1.23, 1.24 (1H each, d, J=6.9 Hz)], an olefinic proton ($\delta_H$ 5.35, br. s), and two aromatic protons [$\delta_H$ 6.60, 6.87 (1H each, s)] (Table 6).

TABLE 6

¹³C and ¹H NMR data of compound 6 (in CDCl₃)[a]

| | 6 | |
|---|---|---|
| Position | $\delta_C$ (ppm) | $\delta_H$ (ppm) |
| 1 | 38.8 | 2.15 (1H, m) |
| | | 1.33 (1H, m) |
| 2 | 19.4 | 1.72 (1H, m) |
| | | 1.60 (1H, m) |
| 3 | 41.8 | 1.48 (1H, m) |
| | | 1.19 (1H, m) |
| 4 | 33.4 | |
| 5 | 44.9 | 1.39 (1H, m) |

TABLE 6-continued $^{13}$C and $^1$H NMR data of compound 6 (in CDCl$_3$)$^a$

| Position | $\delta_C$ (ppm) | $\delta_H$ (ppm) |
|---|---|---|
| 6 | 21.9 | 1.65 (2H, m) |
| 7 | 35.3 | 2.93 (1H, brq, J = 7.5 Hz) |
| 8 | 131.6 | |
| 9 | 148.8 | |
| 10 | 38.0 | |
| 11 | 110.8 | 6.60 (1H, s) |
| 12 | 150.9 | |
| 13 | 131.6 | |
| 14 | 127.1 | 6.87 (1H, s) |
| 15 | 27.0 | 3.08 (1H, sept. J = 6.9 Hz) |
| 16 | 22.8 | 1.24 (3H, d, J = 6.9 Hz) |
| 17 | 22.6 | 1.23 (3H, d, J = 6.9 Hz) |
| 18 | 33.8 | 0.89 (3H, s) |
| 19 | 21.7 | 0.87 (3H, s) |
| 20 | 25.1 | 1.12 (3H, s) |
| 1' | 136.4 | |
| 2' | 120.9 | 5.35 (br s) |
| 3' | 34.8 | 2.23 (1H, m)<br>1.95 (1H, m) |
| 4' | 72.1 | |
| 5' | 31.2 | 1.74 (1H, m)<br>1.56 (1H, m) |
| 6' | 25.0 | 2.19 (2H, m) |
| 7' | 36.6 | 2.92 (1H, m) |
| 8' | 17.0 | 0.93 (3H, d, J = 6.9 Hz) |
| 9' | 16.9 | 0.95 (3H, d, J = 6.9 Hz) |
| 10' | 46.3 | 2.21 (2H, m) |

$^a$The assignment was based upon COSY, HSQC, and HMBC experiments.

Those data suggested that 6 was a derivative of ferruginol (14) (Tezuka, 1998) exhibiting typical signals of ferruginol: an isopropyl group attached to a phenyl group; two para aromatic protons and a typical H$_\beta$-1 proton; as well as three singlet methyl groups (Kazuko, 2006). Therefore, the other moiety of compound 6 was a cyclic monoterpene having a tri-substituted double bond ($\delta_C$ 136.4, 120.9), an isopropyl group, and an oxygenated carbon, suggesting it to be menth-1-en-4-ol. An HMBC experiment revealed long-range couplings from H$_2$-10' at $\delta_C$ 46.3 to C-6, C-7, C-2' and C-6', establishing the linkage between ferruginol and menth-1-en-4-ol. The stereochemistry of compound 6 established by NOESY experiment (Kazuko, 2006; Hsieh, 2006). Thus the structure of 7-(menth-1-en-4-ol)-ferruginol was established as compound 6. Recently, abietane-type diterpenes with novel skeletons, such as diterpenes attached to sesquiterpenes (Kazuko, 2006; Hsieh, 2006; Kazuko & Kentaro, 2006), dimeric diterpenes (Shigenobu, 2004), and monoterpenes (Wu, 2010) were reported from the bark and heartwood of *Cryptomeria japonica* (L. f.) D. Don, the fruits of *C. fortunei* Hooibr. ex Otto & A. Dietr., and the bark of *Calocedrus macrolepis* var. formosana (Florin) W. C. Cheng & L. K. Fu. Compound 6 has a new ferruginol-menthol skeleton and is named as salviniol (6) because of the plant source *Salvinia*.

Example 3

All the isolated compounds (1-50) were further tested for their cytotoxicity against human exocrine pancreatic cancer (PANC-1 and BxPC-3), non-small cell lung cancer (A549), prostate cancer (PC-3), breast cancer (MDA-MB-231), leukemia (HL-60), and normal lung cells (MRC-5). Among all tested compounds, 16 abietane diterpenes (6-17 and 19-22) demonstrated only moderate or weak activities against all tumor cells (Table 7).

TABLE 7

Cytotoxic activity of 17 abietane diterpenes against various human tumor cell lines (GI$_{50}$) (μM)

| Compound | A549 | PC-3 | HL-60 | PANC-1 | BxPC-3 | MDA-MB-231 | MRC-5 |
|---|---|---|---|---|---|---|---|
| 6 | 62.91 ± 9.63 | 54.19 ± 5.90 | 48.05 ± 10.86 | 60.44 ± 16.17 | 87.28 ± 24.51 | 75.0 ± 1.37 | 58.41 ± 6.83 |
| 7 | 9.10 ± 2.47 | 8.39 ± 0.86 | 13.33 ± 5.62 | 22.59 ± 4.18 | 37.28 ± 7.44 | >100 | 24.75 ± 4.73 |
| 8 | 11.07 ± 3.16 | 13.17 ± 2.03 | 11.45 ± 3.13 | 23.08 ± 9.16 | 25.0 ± 13.19 | N/A | 20.01 ± 5.14 |
| 9 | 84.52 ± 18.73 | >100 | 92.78 ± 9.98 | >100 | >100 | N/A | >100 |
| 10 | 86.50 ± 9.54 | N/A | N/A | N/A | N/A | N/A | N/A |
| 11 | 21.21 ± 6.21 | N/A | N/A | N/A | N/A | N/A | N/A |
| 12 | 35.04 ± 6.20 | 41.03 ± 7.90 | 35.26 ± 0.63 | 43.14 ± 8.32 | 45.01 ± 8.33 | N/A | 40.19 ± 0.91 |
| 13 | 79.8 ± 2.18 | >100 | 68.64 ± 13.46 | 87.94 ± 11.18 | 36.08 ± 1.50 | N/A | >100 |
| 14 | 30.67 ± 5.22 | 56.45 ± 16.51 | 27.33 ± 8.95 | 41.13 ± 14.11 | 21.14 ± 0.51 | N/A | 40.01 ± 7.74 |
| 15 | 75.11 ± 7.04 | 85.61 ± 5.30 | 75.19 ± 1.02 | 78.24 ± 13.46 | 74.73 ± 11.09 | N/A | 70.49 ± 7.21 |
| 16 | 53.79 ± 9.65 | 58.12 ± 3.28 | 66.52 ± 0.04 | 46.71 ± 10.98 | 37.50 ± 4.01 | N/A | 59.25 ± 7.56 |
| 17 | 42.22 ± 3.89 | 43.60 ± 11.88 | 50.01 ± 15.23 | 37.53 ± 5.72 | 36.42 ± 8.08 | N/A | 55.36 ± 4.94 |
| 18 | (−) | (−) | (−) | (−) | (−) | N/A | (−) |
| 19 | 24.89 ± 5.94 | 18.97 ± 5.34 | 23.27 ± 6.66 | 32.15 ± 2.75 | 20.54 ± 2.00 | N/A | 20.39 ± 3.36 |
| 20 | 30.14 ± 3.64 | 27.07 ± 11.76 | 36.33 ± 7.14 | 52.55 ± 18.84 | 51.04 ± 10.44 | N/A | 45.70 ± 2.32 |
| 21 | 47.96 ± 7.75 | 46.32 ± 6.60 | 30.03 ± 8.30 | 51.34 ± 10.04 | 41.74 ± 2.92 | N/A | 40.19 ± 2.06 |
| 22 | 93.75 ± 21.39 | N/A | N/A | N/A | N/A | N/A | N/A |

Note:
GI$_{50}$ (mean ± S.D.) refers to the concentration required to have 50% cell-growth inhibition; (−) indicates that the isolated is inactive (negative at 100 or GI$_{50}$ >100 μM); N/A: no data available.

14-deoxycoleon U (7) and montbretol (8) were found to be the best activities and high selective, especially, no toxic against normal cell. The suppressive effects of salviniol (6) and montbretol (8) on human PANC-1 and BxPC-3 pancreatic cancer cell proliferation were investigated, and both could inhibit human pancreatic cancer cell proliferation in a dose-dependent manner (FIG. 3).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

USDA, Animal and plant health inspection service: giant salvinia-pest alert. APHIS 81-35-006, 2000. Available: http://www.invasive.org/publications/aphis/gsalvini.pdf. Accessed in September 2012.
Abbasi, et al., Environ Conserv. 13:235-241, 1986.
Areche, et al., Briq. J Pharm Pharmacol. 61(12):1689-97, 2009.
Avupati, et al., Bioorg Med Chem Lett. 22(2):1031-5, 2012.
Ayhan, et al., J Nat Prod. 55(4):441-5, 1992.
Bang, et al., Arch Pharm Res. 25(4):438-440, 2002.
Barrett, et al., Sci Amer. 260:90-7, 1989.
Benjamin, Magn Reson Chem. 41(9):741-746, 2003.
Brubaker, et al., J Med Chem. 29(6):1094-9, 1986.
Chantiratikul, et al., Res J Biol Sci. 4(10):1113-7, 2009.
Choudhary, et al., Phytochemistry. 69:1018-23, 2008.
DellaGreca, et al., J Nat Prod. 67:1492-5, 2004.
Ding, et al., Chem Pharm Bull. 47:652-5, 1999.
Elisa, et al., Annali di Chimica, 59(6):510-7, 1969.
Fang, et al., J Chem Res-S. 9:350-1, 1986.
Fielding, et al., J Chem Soc. 2(1):151-63, 2002.
Finlayson, Australia Aquat Bot., 18:257-262, 1984.
Fraga, et al., J Agric Food Chem. 53(13):5200-5206, 2005.
Fronza, et al., Bioorg Med Chem Lett. 19(16):4876-81, 2011.
Fujita, et al., Biosci Biotech Biochem. 60(4):732-5, 1996.
Guerrero, et al., J Nat Prod. 69(12):1803-5, 2006.
Hans-Dieter, et al., Phytochemistry. 38(3):569-71, 1995.
Hsieh, et al., J Nat Prod. 69:1611-3, 2006.
Huang, et al., Helv Chim Acta. 89(6):1169-75, 2006.
Janicsak, et al., Nat Prod Comm. 6(5):575-9, 2011.
Jonathan, et al., J Nat Prod. 52(3):571-5, 1989.
Julien, M. H.; Hill, M. P.; Tipping, P. W. Salvinia molesta D. S. Mitchell (Salviniaceae). In Biological control of tropical weeds using arthropods. Cambridge University Press: 2009.
Kazuko, et al., Chem Pharm Bull. 54(4):574-8, 2006.
Kazuko, et al., Chem Pharm Bull. 54(3):315-9, 2006.
Kuo, et al., Helv Chim Acta. 85(9):2657-63, 2002.
Kuo, et al., Phytochemistry, 49(8):2453-5, 1998.
Kusumoto, et al., J Chem Ecol. 35:635-42, 2009.
Lin, et al., Cancer Res. 68(16):6634-42, 2008.
Lin, Zhonghua Yaoxue Zazhi. 45(1):61-8, 1993.
Mahato, et al., Phytochemistry. 37(6):1517-5, 1994.
Miyazawa, et al., J Agric Food Chem. 44:1543-7, 1996.
Moozhiyil, et al., J Econ Bot. 40(3):375-83, 1986.
Moujir, et al., Phytotherapy Res. 10(2):172-4, 1996.
Mustafa, et al., Tetrahedron. 19(11):1831-9, 1963.
Narasimhulua, et al., Nat Prod Res. 24(15):1390-4, 2010.
Oiso, et al., Chem. Pharm. Bull. 49(1):126-128, 2001.
Room, et al., Ecol Evol. 5:74-9, 1990.
Room, et al., J Appl Ecol. 23:1013-28, 1986.
Sairafianpour, et al., J Nat Prod. 64:1398-403, 2001.
Schooler, et al., Nature, 470:86-9, 2011.
Shigenobu, et al., Chem Pharm Bull. 52(3):354-8, 2004.
Siddiuui, et al., J Asian Nat Prod Res. 9(4):407-14, 2007.
Slamenova, et al., Basic Clin Pharmacol Toxicol. 94(6):282-90, 2004.
Srilaxmi, et al., BMC Pharm. 10:13, 2010.
Tamura, et al., Bioorg Med Chem Lett. 20(6):1837-9, 2010.
Tanaka, et al., Chem. Pharm. Bull. 55(6):899-901, 2007.
Tan, et al., Biochem Syst Ecol. 40:4-5, 2012.
Tezuka, et al., Chem Pharm Bull. 46(1):107-12, 1998.
Toyota, et al., Chem. Pharm. Bull. 50(4):508-514, 2002.
Topcu, et al., Pharm Biol, 46(3):180-4, 2008.
Ulubelen, et al., J Nat Prod. 55(4):441-444, 1992.
Ulubelen, et al., Pharma Biol. 37(2):148-51, 1999.
Wu, et al., J Asian Nat Prod Res. 12(5):382-7, 2010.
Xiang, et al., J Asian Nat Prod Res. 10:1081-5, 2008.
Xiang, et al., Chinese Chem Lett. 13(2):141-2, 2002.
Xu, et al., Nat Prod Comm. 61(1):3-5, 2011.
Yao, et al., J Nat Prod. 71:1242-6, 2008.
Yu, D. Q.; Yang, J. S. Handbook of Analytical Chemistry; Chemical Industry Press: Beijing, 1999.
Zhang, et al., Phytochemistry. 69:2070-80, 2008.
Zhao, et al., J Nat Prod. 74(6):1392-1400, 2011.

The invention claimed is:

1. A method of treating cancer in a patient in need thereof, comprising administering to the patient a pharmaceutical composition comprising an effective amount of a compound of the formula:

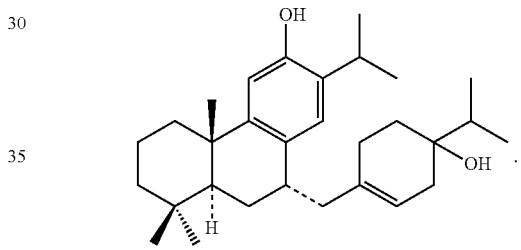

2. The method of claim 1, wherein the cancer is melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplastic syndrome, multiple myeloma, transitional cell carcinoma, neuroblastoma, plasma cell neoplasms, Wilm's tumor, or hepatocellular carcinoma.

3. The method of claim 1 wherein said patient is further administered a distinct cancer therapy.

4. The method of claim 1, wherein the compound is isolated from a plant in the Salviniaceae family.

5. The method of claim 4, wherein the compound is isolated from a plant in the Salvinia genus.

6. The method of claim 4, wherein the compound is isolated from S. auriculata, S. biloba, S. cucullata, S. cyathiformis, S. hastate, S. herzogii, S. minima, S. molesta, S. natans, S. nymphellula, S. oblongifolia, S. radula, S. rotundifolia, or S. sprucei.

7. The method of claim 4, wherein the compound is isolated from a plant in the Azolla genus.

8. The method of claim 1, wherein the pharmaceutical composition further comprises an excipient.

* * * * *